United States Patent
Barredo Fuente et al.

(10) Patent No.: US 6,558,921 B1
(45) Date of Patent: May 6, 2003

(54) PROMOTERS OF THE GENES GLUTAMATE DESHYDROGENASE, β-N-ACETYLHEXOSAMINIDASE AND γ-ACTIN AND THEIR USE IN FILAMENTOUS FUNGI EXPRESSION, SECRETION AND ANTISENSE SYSTEMS

(75) Inventors: Jose Luis Barredo Fuente, Leon (ES); Marta Rodriguez Saiz, Pontevedra (ES); Alfonso J. Collados de la Vieja, Leon (ES); Migeul Angel Moreno Valle, Leon (ES); Francisco Salto Maldonado, Madrid (ES); Bruno Diez Garcia, Leon (ES)

(73) Assignee: Antibioticos, S.A., Leon (ES)

( * ) Notice: Subject to any disclaimer, the term of this patent is extended or adjusted under 35 U.S.C. 154(b) by 211 days.

(21) Appl. No.: 09/631,022

(22) Filed: Aug. 2, 2000

Related U.S. Application Data

(62) Division of application No. 09/171,337, filed as application No. PCT/ES98/00056 on Mar. 5, 1998, now Pat. No. 6,330,095.

(30) Foreign Application Priority Data

Mar. 5, 1997 (ES) ................................ 9700482

(51) Int. Cl.$^7$ ............................. C12P 1/02; C12P 21/02; C12N 15/80; C07K 14/37; C07K 21/04
(52) U.S. Cl. ..................... 435/69.1; 435/41; 435/71.1; 435/320.1; 435/471; 435/476; 435/243; 435/254.1; 435/254.11; 435/254.3; 435/254.5; 435/254.21; 435/484; 435/455; 435/475; 435/483; 530/371; 530/350; 536/22.1; 536/23.1; 536/23.74; 536/24.1; 536/25.3
(58) Field of Search .................. 435/41, 69.1, 71.1, 435/89, 91.1, 320.1, 471, 476, 243, 254.1, 254.11, 254.3, 254.5; 530/371; 536/22.1, 23.1, 23.74, 24.1, 25.3

(56) References Cited

U.S. PATENT DOCUMENTS 6,300,095 B1 * 10/2001 Barredo Fuente et al. . 435/69.1

FOREIGN PATENT DOCUMENTS

EP 0225078 6/1987
EP 0215539 8/1987

OTHER PUBLICATIONS

Bogati, M. et al. "NAPD–Specific Gluatmate Dehydrogenase of *Penicillium chrysogenum* Has a Homohexamer Structure" *J. Basic Microbiol.* vol. 36 No. 5 (1996) pp 3671–375.
Shen, H–D, et al. "Molecular Cloning of cDNA Coding for the 68kDa Allergen of *Penicillium notatum* using MoAbs" *Clinical and Experimental Allergy* vol. 25 (1995) pp 350–356.
Fidel, S. et al. "*Aspergillus nidulans* Contains a Single Actin Gene Which Has Unique Intron Locations and Encodes a γ–Actin" *Gene* vol. 70 (1988) pp. 283–293.
Jaklitsch, W.M. et al. "Glutamate Pools and Glutamate Dehydrogenase Regulation in Relation to Penicillin . . . *Penicillium chrysogenum*" *Experimental Mycology* vol. 9 (1985) pp 310–317.
Frederick, G.D. et al. "Distant Upstream Regulatory Sequences Control the Level of Expression of the am (GDH) Locus of *Neurospora crassa*" *Current Genetics* vol. 18 (1990) pp 53–58.
Hawkins, A.R. et al. "Nucleotide Sequence and Regulation of Expression of the *Aspergillus nidulans* ghdA Gene . . . Dehydrogenase" *Mol. Gen. Genet.* vol. 218 (1989) pp 105–111.
Posci, I. et al. "The Formation of N–Acetyl–β–D–Hexosaminidase is Repressed by Glucose in *Penicillium chroysogenum*" *J. Basic Microbiol.* vol. 33 (1993) pp 259–267.
Gutierrez, S. et al. "Expression of the cefG Gene is Limiting for Cephalosporin Biosynthesis in *Acremonium chrysogenum*" *Appl. Microbiol. Biotechnol* vol. 48 (1997) pp 606–614.

* cited by examiner

*Primary Examiner*—David Guzo
*Assistant Examiner*—David A. Lambertson
(74) *Attorney, Agent, or Firm*—Ladas & Parry

(57) ABSTRACT

An isolated DNA having the promoter sequence of the hex gene of *P. chrysogenum* or a DNA fragment that is hybridizable to the complement of the promoter sequence under stringent conditions and is capable of directing expression of DNA downstream of the fragment in *P. chrysogenum*. Also a process for promoting expression of a coding sequence of interest in a microorganism using the isolated DNA and a process to block expression of a gene of interest in a microorganism using the isolated DNA are disclosed.

27 Claims, 6 Drawing Sheets

PROMOTERS OF THE GENES GLUTAMATE DESHYDROGENASE, β-N-ACETYLHEXOSAMINIDASE AND γ-ACTIN AND THEIR USE IN FILAMENTOUS FUNGI EXPRESSION, SECRETION AND ANTISENSE SYSTEMS

This application is a divisional of application Ser. No. 09/171,337 filed on May 14, 1999, now U.S. Pat. No. 6,300,095, which is International Application PCT/ES98/00056 filed on Mar. 5, 1998 and which designated the U.S., claims the benefit thereof and incorporates the same by reference.

FIELD OF THE INVENTION

The invention relates to the technical field of the expression of the gdh and hex genes of *Penicillium chrysogenum* and of the act gene also of *P. chrysogenum* and of *Acremonium chrysogenum*. From analysis of the nucleotide sequence of said genes the existence of a promoter region which includes the translation initiation site, and which can be used to construct powerful expression and secretion vectors that are useful both for *P. chrysogenum* and for *A. chrysogenum* and related species, is deduced. In addition, these promoters can be used to block gene expression by means of antisense constructs. The expression of other genes in filamentous fungi can be directed under the control of the aforesaid promoters, with the production of antibiotics and/or proteins inherent therein being increased.

PRIOR ART

*P. chrysogenum* and *A. chrysogenum* are filamentous fungi which are of industrial interest because of their ability to produce penicillin and cephalosporin, respectively. During the last decade there has been considerable development of genetic manipulation techniques applicable in both microorganisms. The techniques for genetic manipulation of *P. chrysogenum* and *A. chrysogenum* include the transformation of protoplasts with vectors which use the phleomycin resistance gene (hereinafter called ble$^R$ gene) (Kolar, M. et al. (1988), Gene 62, 127–134) as a selection marker, as well as the expression of additional intact copies of genes of interest and the replacement of the promoter of the gene in question by another promoter which is able to improve its expression. The expression of homologous genes in fungi such as *P. chrysoqenum* or *A. chrysogenum* can be negatively regulated, whereas in the case of heterologous genes it is possible that their promoter may not be efficiently recognized by the said fungi. With the aim of avoiding these problems, genes were identified and cloned which are expressed constitutively and in which the said expression preferably does not show negative catabolic regulation, called hereinafter strong promoters. In general it is considered that the high-expression genes have signals in the promoter region which facilitate high transcription levels and which play a fundamental rôle in functions implicated in primary cellular metabolism. These genes include: the genes which code for NADP-dependent glutamate dehydrogenase (EC.1.4.1.4) (hereinafter called gdh gene), β-N-acetylhexosaminidase (EC.3.2.1.52) (hereinafter called hex gene) and γ-actin (hereinafter called act gene).

There are earlier references to the gdh, hex and act genes from microorganisms other than those which are used in the present invention. The most relevant bibliography includes: (I) the nucleotide sequence of the gdh gene of the fungus *Neurospora crassa* (Kinnaird, J. H. and Fincham, J. R. S. (1983), Gene 26, 253–260) as well as the regulation of the expression of the gdhA gene of *Aspergillus nidulans* (Hawkins, A. R. et al. (1989), Mol. Gen. Genet. 418, 105–111), (II) the cloning and expression of the hex1 gene of *Candida albicans* (Cannon, R. D. et al. (1994), J. Bacteriol. 2640–2647) and (III) the characterization of the act gene of *A. nidulans* (Fidel, S. et al. (1988), Gene 70, 283–293). The expression of heterologous genes in *P. chrysogenum* using the promoters of the pcbC or penDE genes was described by Cantwell, C. A. et al. in 1992 (Proc. R. Soc. London Ser. B 248, 283–289). In addition, the expression of heterologous genes in *A. chrysogenum* using the promoters of the β-isopropyl malate dehydrogenase gene (Japanese Patent Laid Open Publication No. 80295/1989) and glyceraldehyde 3-phosphate dehydrogenase gene (European Patent Application 0376226A1/1989) has also been described.

The inactivation of gene expression in industrial strains is sometimes necessary for the elimination of undesirable enzyme activities. Owing to the fact that the level of ploidy of many industrial strains makes it difficult in most cases to block expression by direct gene disruption, it is necessary to use systems for inactivation of expression which are independent of the level of ploidy. The development of antisense constructs expressed under the control of strong promoters makes interruption of gene expression possible. Constructs of this type are especially useful in industrial strains owing to the fact that their levels of ploidy (Künkel et al. (1992) Appl. Microbiol. Biotech. 36, 499–502) make it difficult to obtain complete gene inactivation. The use of antisense constructs for blocking enzyme activities has been described in yeasts (Atkins, D. et al. (1994), Biol. Chem. H-S 375, 721–729) and plants (Hamada, T. (1996), Transgenic Research 5, 115–121; John, M. E. (1996) Plant Mol. Biol. 30, 297–306). The hex promoter has the special feature of coding for an extracellular enzyme, which allows it to be used for the expression of extracellular proteins.

There are no citations in the prior art, however, which describe either the gene sequences of the filamentous fungi used in the present invention or those of the enzymes synthesized by the expression thereof. Nor is there any description in said Prior Art of the use of the strong promoters of the genes of the fungi described in the present invention for the expression, secretion or inactivation of gene expression.

DETAILED DESCRIPTION OF THE INVENTION

The use of strong promoters to overexpress certain genes can lead to improvement in the production of penicillin or cephalosporin, and also to the synthesis of new antibiotics derived from the latter.

This invention describes a new process for obtaining strains of *P. chrysogenum* and *A. chrysogenum* with the ability to express homologous or heterologous genes under the control of strong promoters. The characterization and subsequent use of the promoters corresponding to the genes which code for NADP-dependent glutamate dehydrogenase (EC.1.4.1.4)—gdh gene—of *P. chrysogenum*, β-N-acetylhexosaminidase (EC.3.2.1.52)—hex gene—of *P. chrysogenum* and γ-actin—act gene—of *P. chrysogenum* and *A. chrysogenum* are described. The use of said promoters to overexpress genes related to the biosynthesis of penicillin and/or cephalosporin in the above-mentioned strains is one of the aims of the present invention. These promoters can also be used to block gene expression by means of antisense constructs.

The present invention is based on *P. chrysogenum* and *A. chrysogenum* as nucleic acid donors. Once the genomic DNA had been purified, DNA libraries of both microorganisms were constructed as described in Examples 1 and 4, and they were screened with: (I) synthetic oligonucleotides corresponding to the gdh gene of *N. crassa* in order to clone the homologous gene of *P. chrysogenum*, (II) combinations of oligonucleotides synthesized on the basis of the amino terminal sequence of the enzyme β-N-acetylhexosaminidase in order to clone the hex gene of *P. chrysogenum* and (III) a fragment of the act gene of *A. nidulans* in order to clone the homologous genes of *P. chrysogenum* and *A. chrysogenum*. The clones purified by virtue of their ability to generate positive hybridization with the corresponding probe were subsequently analysed, the presence of the genes sought being determined.

The gdh gene of *P. chrysogenum* was identified in a 7.2 kb EcoRI fragment and in two BamHI fragments of 2.9 and 1.5 kb respectively. The restriction map of the DNA region which includes it is shown in FIG. 1. The 2,816 nucleotide sequence (SEQ ID NO:1) was then determined, which includes an open reading frame (ORF) with a very marked preferential codon usage pattern, the ATG translation initiation codon of which was found in position 922 and the TAA translation termination codon in position 2,522. The presence of 2 introns of 159 bp and 56 bp was also determined between positions 971–1130 and 1262–1318 respectively. Said ORF codes for a protein of 49,837 Da, with an isoelectric point of 6.18, the 461 amino acid sequence of which (SEQ ID NO:5) has 72.4% identity with the amino acid sequence of the NADP-dependent glutamate dehydrogenase enzyme of *N. crassa*. In the promoter region there are found pyrimidine-rich zones similar to those which appear in highly expressed genes, as well as two presumed TATA boxes (this box is found in certain promoters of fungi 30 to 50 bp upstream from the site of transcription initiation) (Davis, M. A. and Hynes, M. J. (1991), More Gene Manipulations in Fungi, Academic Press,. San Diego, Calif.) and a CCAAT box (which is found in about 30% of promoters of eukaryotic genes 50 to 200 bp upstream from the site of transcription initiation) (Bucher, P. (1990) J. Mol. Biol. 212: 563–578). This promoter was then used to express in *P. chrysogenum* and *A. chrysogenum* the *E. coli* gene which codes for β-galactosidase (hereinafter called lacZ gene) and the ble$^R$ gene of *S. hindustanus*. The plasmids pSKGSu and pALfleo7 (FIG. 5) were constructed for this purpose, as described in Example 1. From the results obtained it is deduced that the gdh promoter (hereinafter called Pgdh) is able to control the expression of the heterologous lacZ and ble$^R$ genes both in *P. chrysogenum* and *A. chrysogenum* and also in *E. coli*.

The development of antisense constructs expressed under the control of strong promoters makes the interruption of gene expression possible. The plasmid pALP888 (FIG. 5) was constructed for this purpose, as described in Section 1.3 of Example 1. The results obtained confirm the possibility of totally or partially blocking undesirable enzyme activities in *P. chrysogenum* by the use of antisense constructs using Pgdh.

The hex gene of *P. chrysogenum* was identified in a 3.2 kb SacI fragment and in a 2.1 kb SalI fragment. The restriction map of the DNA region which includes the hex gene is shown in FIG. 2. The 5,240 nucleotide sequence (SEQ ID NO:2) was then determined, confirming the existence of two ORFs with a very marked preferential codon usage pattern, one of which matched the hex gene. The ATG translation initiation codon of the hex gene was found in position 1,324 and the TGA termination codon in position 3,112. Said ORF has no introns and codes for a protein of 66,545 Da, with an isoelectric point of 5.34, the 596 amino acid sequence of which (SEQ ID NO:6) has 49.0% identity with the amino acid sequence of the β-N-acetylhexosaminidase enzyme of *Candida albicans*. In addition, the deduced amino acid sequence includes the polypeptides determined chemically from the purified enzyme in positions 19–40 and 99–120. In the promoter region there are found two pyrimidine-rich zones, a presumed TATA box and the CAAT box. This promoter was then used to express the ble$^R$ gene of *S. hindustanus* in *P. chrysogenum*. The plasmid pALP480 (FIG. 6) was constructed for this purpose, as described in Example 2. From the results obtained it is deduced that the hex promoter (hereinafter called Phex) is able to control the expression of the heterologous ble$^R$ gene in *P. chrysogenum*. In addition, the fact that the enzyme β-N-acetylhexosaminidase is a protein abundantly secreted by *P. chrysogenum* to the culture medium makes it possible to use the hex gene for the expression and secretion of homologous or heterologous proteins in *P. chrysogenum* or related filamentous fungi. The genes to be expressed can be fused in a reading frame with the promoter region, including the secretion signal sequence of the hex gene, or else they can be fused in a reading frame with the complete hex gene.

The act gene of *P. chrysogenum* (hereinafter called actPc) was identified in a 5.2 kb BamHI fragment, a 4.9 kb EcoRI fragment and a 5.9 kb HindIII fragment. The restriction map of the DNA region which includes the actPc gene is shown in FIG. 3. Once the 2,994 nucleotide sequence (SEQ ID NO:3) had been determined, the existence of an ORF with a very marked preferential codon usage pattern was confirmed. The ATG translation initiation codon was found in position 494 and the TAA termination codon in position 2,250. Said ORF has 5 introns and codes for a protein of 41,760 Da, with an isoelectric point of 5.51, the 375 amino acid sequence of which (SEQ ID NO:7) has 98.1% identity with the amino acid sequence of the γ-actin protein of *A. nidulans*. In the promoter region there are found two pyrimidine-rich zones, a presumed TATA box and four CAAT boxes. This promoter was then used to express the ble$^R$ gene of *S. hindustanus* in *P. chrysogenum*. The plasmid pALPfleo1 (FIG. 6) was constructed for this purpose, as described in Example 3. From the results obtained it is deduced that the act promoter of *P. chrysogenum* (hereinafter called PactPc) is able to control the expression of the heterologous ble$^R$ gene in *P. chrysogenum*.

The act gene of *A. chrysogenum* (hereinafter called actAc) was identified in SalI fragments of 2.4 and 1.1 kb, a 3.9 kb SmaI fragment and an 8.7 kb HindIII fragment. The restriction map of the DNA region which includes the actAc gene is shown in FIG. 4. The 3,240 nucleotide sequence determined (SEQ ID NO:4) confirmed the existence of an ORF with a very marked preferential codon usage pattern. The ATG translation initiation codon was found in position 787 and the TAA termination codon in position 2,478. Said ORF has 5 introns and codes for a protein of 41,612 Da, with an isoelectric point of 5.51, the 375 amino acid sequence of which (SEQ ID NO:8) has 98.4% and 98.1% identity with the amino acid sequences corresponding to the γ-actin proteins of *A. nidulans* and *P. chrysogenum*, respectively. In the promoter region there are found pyrimidine-rich zones and a CAAT box, the existence of a TATA box not being observed. This promoter was then used to express the ble$^R$ gene of *S. hindustanus* in *A. chrysogenum*. The plasmid pALCfleo1 (FIG. 6) was constructed for this purpose, as described in Example 4. From the results obtained it is deduced that the act promoter of *A. chrysogenum* (hereinafter called PactAc) is able to control the expression of the heterologous ble$^R$ gene in *A. chrysogenum*.

In all cases, the expression of the heterologous gene in *P. chrysogenum* or *A. chrysogenum* under the control of the fungal promoter was achieved by fusing the said gene in the correct reading frame. Although the lacZ and ble$^R$ genes were expressed by way of example, it would be possible in the same way to express genes which code for enzymes involved in the biosynthesis of penicillin: pcbAB (α-aminoadipyl-cysteinyl-valine synthetase), pcbC (isopenicillin N synthase), penDE (acyl-CoA:6-APA acyltransferase), pcl (phenylacetyl-CoA ligase), etc.; or of cephalosporin: pcbAB (α-aminoadipyl-cysteinyl-valine synthetase), pcbC (isopenicillin N synthase), cefD (isopenicillin N isomerase), cefEF (deacetoxycephalosporin C synthase/hydroxylase), cefG (deacetylcephalosporin C acetyltransferase), etc. The gene to be expressed may have been obtained by different methods: isolated from chromosome DNA, cDNA synthesized from mRNA, synthesized chemically, etc. The fundamental processes for correct promoter-gene fusion are described in Sambrook, J. et al. (1989), Molecular Cloning: A Laboratory Manual, Cold Spring Harbor Laboratory, Cold Spring Harbor, N.Y., USA, and Ausubel et al. (1987), Current Protocols in Molecular Biology, John Wiley & Sons, New York, USA.

*P. chrysogenum* and *A. chrysogenum* were used as host strains, but any related strain or mutant strain derived from them can be used. The process employed for the production of protoplasts and transformation of *P. chrysogenum* was based on that described by Cantoral et al. in 1987 (Biotechnology 5: 494–497) and Díez et al. in 1987 (Curr. Genet. 12: 277–282) and is described in Example 1. The production of protoplasts and transformation of *A. chrysogenum* are described in Example 4. In both cases use was made of the antibiotic phleomycin as selection marker and the plasmids pALfleo7, pALP480, pALPfleo1 or pALCfleo1, which are carriers of the ble$^R$ gene expressed under the control of Pgdh, Phex, PactPc and PactAc, respectively. It would be possible, however, to use any marker which can selectively separate the transformant strains from the others, which are not.

The transformant may be grown in culture media containing carbon and nitrogen sources which can be assimilated. Examples of carbon sources are glucose, sucrose, lactose, starch, glycerine, organic acids, alcohols, fatty acids, etc., used alone or in combination. Examples of nitrogen sources would be peptone, malt extract, yeast extract, corn steep liquor, gluten, urea, ammonium salts, nitrates, NZ-amine, ammonium sulphate, etc., used alone or in combination. Inorganic salts which can be used as components of the culture medium include phosphates (for example potassium phosphate), sulphates (for example sodium sulphate), chlorides (for example magnesium chloride), etc., and iron, magnesium, calcium, manganese, cobalt, etc., can be used as ions. The cultural conditions such as incubation temperature, pH of the culture medium, aeration, incubation time, etc., must be selected and adjusted in accordance with the strain used. In general terms, however, fermentation is carried out for a period of 4 to 14 days under aerobic conditions at a temperature between 20° C. and 30° C. and a pH between 5 and 9.

In summary, the present invention includes: (I) DNA fragments which contain the promoters of the gdh, hex and act genes of *P. chrysogenum* and of the act gene of *A. chrysogenum*, (II) plasmids which incorporate the aforesaid promoters together with their translation initiation site, (III) plasmids in which a homologous or heterologous structural gene or an antisense DNA fragment is situated, under the control of the said promoters, (IV) *P. chrysogenum* or *A. chrysogenum* strains transformed with said plasmids, (VI) transformant strains able to express the structural gene or the antisense DNA situated in the plasmid under the control of the promoter and (VII) transformant strains able to secrete homologous or heterologous extracellular proteins under the control of the Phex.

The following examples describe the present invention in detail, without limiting its scope.

EXAMPLE 1

1.1. Cloning and Characterization of the gdh Gene of *P. chrysogenum*.

With the aim of cloning the gdh gene of *P. chrysogenum*, a DNA library was constructed in the phage vector λGEM12, using established procedures (Sambrook, J. et al. (1989), Molecular Cloning: A Laboratory Manual, Cold Spring Harbor Laboratory, Cold Spring Harbor, N.Y., USA). To this end, the total DNA of the fungus (purified by the method described by Barredo et al. (1994) Spanish Patent P9400931) was partially digested with Sau3AI and the fragments of about 20 kb were purified in a sucrose gradient (10–40%). These fragments were ligated with the arms of the vector, which had previously been digested with BamHI and purified, and the ligation mixture was then packaged in vitro using the Gigapack II Gold (Stratagene) system in accordance with the manufacturer's instructions. The packaging reaction, resuspended in 500 μl of SM, was used to make infections of *E. coli* LE392, in order to titrate the number of phages present, and of *E. coli* NM539, with the aim of determining the percentage of recombinant phages. *E. coli* NM539 is a lysogenic strain of the phage P2 and only produces lysis plaques when the phage which infects it lacks the dispensable central region. The phage titre was found to be 132 pfu/μl (a total of 66,000 pfu) in *E. coli* LE392 and 113 pfu/μl (a total of 56,500 pfu) in *E. coli* NM539. This meant that about 85% of the phages were carrying an exogenous DNA insert. The number of recombinant phages needed to make up a complete DNA library was calculated with the equation: N=ln(1−p)/ln(1−f), where "p" is the desired probability, "f" is the proportion of the genome of the selected organism which is contained in a recombinant, and "N" is the number of recombinants needed. Assuming that the genome of *P. chrysogenum* is contained in about 30,000 kb (Fierro et al. (1993), *Mol. Gen. Genet.* 241: 573–578) and that the average of the packaged inserts was 18 kb (in spite of the fact that sizes around 20 kb had been selected), a *P. chrysogenum* DNA library had been obtained with 99.999% probability with the number of recombinant phages obtained. After this series of theoretical verifications had been carried out, *E. coli* NM539 was infected and the complete DNA library was spread on 5 Petri dishes of 150 mm diameter (about 11,300 pfu/Petri dish), collected in 50 ml of SM plus 2.5 ml of chloroform, and kept at 4° C. In this way a sufficient and representative volume of recombinant phages (5,300 pfu/μl) ready to be plated out at any time was available.

About 60,000 pfu were spread on 3 Petri dishes of 150 mm diameter and then transferred to nitrocellulose filters (BA85, 0.45 μm, Schleicher & Schuell). Said filters were hybridized using standard protocols (Sambrook, J. et al. (1989), Molecular Cloning: A Laboratory Manual, Cold Spring Harbor Laboratory, Cold Spring Harbor, N.Y., USA) with synthetic oligonucleotides corresponding to the gdh gene of *N. crassa*. A total of 10 positive clones were purified via a second and third hybridization cycle and their DNA was then digested with a series of restriction endonucleases and analysed by the Southern blot technique. In this way the gdh gene was identified in a 7.2 kb EcoRI fragment and in two BamHI fragments of 2.9 and 1.5 kb, respectively. After the corresponding subcloning in the plasmids pBluescript I KS(+) (Stratagene) and pUC13 had been carried out, the plasmids pALP784 and pALP785, which match both orientations of a 2.9 kb Sau3AI-XbaI fragment that includes the gdh gene, were constructed. The restriction map of the DNA region which includes said gene is shown in FIG. 1.

With the aim of determining the nucleotide sequence of the gdh gene, a series of clones were constructed from the plasmids pALP784 and pALP785 by the "Erase a base" method (Promega) and then sequenced by the dideoxynucleotide method using the "Sequenase" test kit (USB), in both cases in accordance with the manufacturer's instructions. The 2,816 nucleotide sequence obtained (SEQ ID NO:1) was analysed with the Geneplot program (DNASTAR), confirming the existence of an ORF with a very marked preferential codon usage pattern. The ATG translation initiation codon was found in position 922 and the TAA termination codon in position 2,522. The presence of 2 introns of 159 bp and 56 bp was also determined between positions 971–1130 and 1262–1318, respectively. Said ORF codes for a protein of 49,837 Da, with an isoelectric point of 6.18, the 461 amino acid sequence of which (SEQ ID NO:5) has 72.4% identity with the amino acid sequence of the NADP-dependent glutamate dehydrogenase enzyme of *N. crassa*.

In the promoter region there are found various pyrimidine-rich zones, although that located between positions 766–796 is the most extensive one. These zones are found in highly expressed genes and are located immediately upstream from the site of transcription initiation. In addition there are two presumed TATA boxes (the consensus sequence of which in fungi is TATAAA) in positions 752 (TATATAATT) and 852 (TATAATTT). These TATA boxes are found in fungi 30 to 50 bp upstream from the site of transcription initiation, so it is most likely that the authentic TATA box is the one situated in position 752, i.e. 42 bp upstream from the site of transcription initiation. The sequence CCAAT is found in the promoter region of about 30% of known eukaryotic genes, situated between 50 and 200 bp upstream from the site of transcription initiation. The CCAAT box is in position 691 in the promoter region of the gdh gene, i.e. about 105 bp upstream from the presumable site of transcription initiation.

1.2. Expression of Control Genes in *P. chrysogenum* and *A. chrysogenum* Under the gdh Promoter The process of transformation and selection of *P. chrysogenum* and *A. chrysogenum* transformants was carried out as described below, depending on their resistance to the antibiotic phleomycin. For this purpose it was necessary to construct the plasmid pALfleo7, which has a size of 5.4 kb and carries the the ble$^R$ gene of *S. hindustanus* expressed under the control of Pgdh as marker in fungi, the chloramphenicol resistance gene as marker in *E. coli* and the polylinker of the plasmid pBC KS (+) (Stratagene).

The procedure used for the production of protoplasts and transformation of *P. chrysogenum* was that described by Cantoral et al. in 1987 (Biotechnology 5: 494–497) and Díez et al. in 1987 (Curr. Genet. 12: 277–282), with slight modifications. First of all, *P. chrysogenum* was grown in the PM defined medium (Anné, J., (1997), Agricultura 25) with addition of 10% yeast extract for 18–21 hours at 25° C., and the mycelium was recovered by filtration through a nylon filter and washed with 3–5 volumes of 0.9% NaCl. After drying it between filter paper, it was resuspended (100 mg/ml) in protoplasts buffer. When the micellar suspension was considered to be homogeneous, a volume of a 4 mg/ml Caylasa solution (Cayla) in protoplasts buffer was added to it and it was incubated for 3 hours at 25° C. with agitation at 100 r.p.m. The appearance of protoplasts was observed microscopically. When most of them had been released, they were separated from the mycelium by filtration through a 30 μm pore nylon filter. The protoplasts suspension was washed 3 times with 0.7 M KCl, centrifuging at 400×g for 3 minutes between washings. The precipitated protoplasts were resuspended in 10 ml of KCM solution and after estimation of their concentration by counting in a Thoma chamber they were adjusted to 1–5×10$^8$ protoplasts/ml with KCM. Next, 100 μl of this solution were carefully mixed with 1–10 μg of DNA plus 10 μl of PCM, and the mixture was incubated in a chilled water bath for 20 minutes. 500 ml of PCM were then added and the mixture was kept at ambient temperature for 20 minutes, after which 600 μl of KCM were added. Transformants were selected on the basis of the ability given by the phleomycin resistance gene present in the plasmids pALfleo7, pALP480 and pALPfleo1 to grow in 30 μg/ml of phleomycin. For this purpose, 200 μl of the transformation reaction were mixed with 5 ml of Czapeck's medium with the addition of sorbitol (1 M) and phleomycin (30 μg/ml), and it was then spread on a Petri dish with 5 ml of the same medium. The plates were incubated at 25° C. until the appearance of transformants was seen (4–8 days).

The procedure used for the production of protoplasts and transformation of *A. chrysogenum* was that described by Gutiérrez et al. (1991), Mol. Gen. Genet. 225: 56–64. First of all, the strain of *A. chrysogenum* was grown in the MMC defined medium for 20–24 hours at 28° C., and the mycelium was recovered by filtration through a nylon filter and washed with 3–5 volumes of 0.9% NaCl. After drying it between filter paper, it was resuspended (50 mg/ml) in protoplasts buffer. When the micellar suspension was considered to be homogeneous, DTT at a final concentration of 10 mM was added to it and it was incubated at 28° C. and 150 r.p.m. for 1 hour. It was then centrifuged at 12,000×g for 15 minutes and the precipitate was resuspended in 20 ml of protoplasts buffer. Next, a volume of a 4 mg/ml Caylasa solution (Cayla) in protoplasts buffer was added and it was incubated for 3 hours at 25° C. with agitation at 100 r.p.m. The appearance of protoplasts was observed microscopically. When most of them had been released, they were separated from the mycelium by filtration through a 25 μm pore nylon filter. The protoplasts suspension was washed 3 times with 0.7 M KCl, centrifuging at 1,000×g for 3 minutes between washings. The precipitated protoplasts were resuspended in 10 ml of NCM buffer and after estimation of their concentration by counting in a Thoma chamber they were adjusted to 1–5×10$^8$ protoplasts/ml. Next, 100 μl of this solution were carefully mixed with 1–10 μg of DNA, and the mixture was kept in a chilled water bath for 20 minutes, after which 1 ml of CCM was added, followed by incubation at ambient temperature for a further 20 minutes. The mixture was centrifuged at 1,000×g for 5 minutes and the sediment was resuspended in 800 μl of NCM buffer. Transformants were selected on the basis of the ability given by the phleomycin resistance gene present in the plasmids pALfleo7 and pALCfleo1 to grow in 10 μg/ml of phleomycin. For this purpose, 200 μl of the transformation reaction were mixed with 5 ml of the TSA medium with addition of sucrose (0.3 M) and phleomycin (10 μg/ml), and it was then spread on a Petri dish with 5 ml of the same medium. The plates were incubated at 28° C. until the appearance of transformants was seen (5–8 days).

In the transformants obtained, an analysis was made of (I) the presence of DNA corresponding to the plasmid used in the transformation, (II) the existence of a transcript corresponding to the control gene and (III) the enzymatic activity corresponding to the gene expressed. Total DNA was obtained in accordance with the conditions described by Barredo et al. in 1994 (Spanish Patent P9400931), and it was then analysed by the Southern blot technique, using the procedure described by Sambrook et al. in 1989 (Molecular Cloning: A Laboratory Manual, Cold Spring Harbor Laboratory, Cold Spring Harbor, N.Y., USA). Total RNA was purified by the method described by Ausubel et al. in 1987 (Current Protocols in Molecular Biology, John Wiley & Sons, New York, USA). The RNA obtained was kept precipitated in ethanol at −20° C. In order to use it, it was recovered by centrifugation at 4° C. and 10,000×g for 20 minutes. The separation of the RNA molecules on the basis of their molecular size was carried out by agarose-formaldehyde electrophoresis. The RNA was then transferred to a nitrocellulose filter and hybridized with the desired probe, all this being done by the method described by Sambrook et al. in 1989 (Molecular Cloning: A Laboratory Manual, Cold Spring Harbor Laboratory, Cold Spring Harbor, N.Y., USA). The appearance of hybridization bands revealed the existence of transcripts and thus the ability to express a bacterial gene in the host fungus: *P. chrysogenum* or *A. chrysogenum*. The β-galactosidase enzyme activity was assessed in the transformants by the method described by Sambrook et al. in 1989 (Molecular Cloning: A Laboratory Manual, Cold Spring Harbor Laboratory, Cold Spring Harbor, N.Y., USA). The expression of the phleomycin resistance gene was assessed on the basis of the level of resistance given to *P. chrysogenum* or *A. chrysogenum* in Czapeck's solid medium after incubation at 25° C. for 7 days.

1.2.1. Expression of the lacZ Gene of *E. coli* in *P. chrysogenum* and *E. coli* Under the Pgdh The lacZ gene of *E. coli* was fused translationally with the Pgdh with the aim of expressing it in *P. chrysogenum*. To this end the lacZ gene was subcloned between the EcoRI and SalI sites of the plasmid pML1 (Carramolino et al. 1989, Gene 77: 31–38), generating the plasmid pMLac. The Pgdh was then introduced between the EcoRI and SmaI sites of pMLac, giving rise to the plasmid pSKG (FIG. 5). Finally, the sulphonamide resistance gene (Carramolino et al. 1989, Gene 77: 31–38) was introduced at the EcoRI site of pSKG, giving rise to the plasmid pSKGSu (FIG. 5). In the *P. chrysogenum* transformants with the plasmid pSKGSu selected for their sulphonamide resistance, analyses were made for the presence of the plasmid by the Southern blot technique and the existence of a transcript corresponding to the lacZ gene by the Northern blot technique. The β-galactosidase enzyme activity was then measured in the transformants which were positive in the two preceding analyses. The transformants efficiently expressed the lacZ gene of *E. coli*, and it was observed that β-galactosidase activity levels were higher in those which contained a copy of the plasmid integrated into their genome than in single-copy transformants which expressed the lacZ gene under the control of the tryptophan C gene promoter (trpC).

The plasmid pSKG was introduced into *E. coli* DH5α (ΔlacZ) with the aim of finding out whether the Pgdh of *P. chrysogenum* was also able to direct the expression of the lacZ gene in *E. coli*. The transformants obtained had the ability to generate blue-coloured colonies after 10 days of incubation at 25° C. in LB medium to which isopropyl-β-D-galactoside (IPTG) and 5-bromo-4-chloro-3-indolyl-β-D-galactoside (X-gal) had been added. This result confirmed that the Pgdh-lacZ construct expresses the β-galactosidase enzyme activity in *E. coli*, although less efficiently than the endogenous lacz gene of *E. coli*.

1.2.2. Expression of the $ble^R$ Gene of *S. hindustanus* in *P. chrysogenum* and *A. chrysogenum* Under the Pgdh The $ble^R$ gene without its promoter region was obtained from the plasmid pUT737 (Mullaney et al. (1985), Mol. Gen. Genet. 199: 37–45) as a 1,100 bp NcoI-ApaI fragment. This fragment was then subcloned in the plasmid pUT713 previously digested with NcoI-ApaI, giving the plasmid pALfleo5. The Pgdh was recovered from pALP25 as a 726 bp EcoRI-BamHI fragment, which was then subcloned in pALfleo5 (previously digested with EcoRI-BamHI) to generate pALfleo6. This last plasmid has a size of 4.2 kb, the $ble^R$ gene expressed under the control of the Pgdh and the ampicillin resistance gene as marker in *E. coli*. With the aim of replacing the latter marker with the chloramphenicol resistance gene, a 1,900 bp EcoRI-NotI fragment which included the Pgdh, $ble^R$ and the terminator of the trpC gene (TtrpC) was purified from pALfleo6 and ligated to the plasmid pBC KS (+) (Stratagene) digested with EcoRI-NotI. This resulted in the plasmid pALfleo7 (FIG. 5), which has a size of 5.4 kb and carries the $ble^R$ gene of *S. hindustanus* under the Pgdh as selection marker in fungi, the chloramphenicol resistance gene as marker in *E. coli* and the polylinker of the plasmid pBC KS (+). The sequencing of the fusion region between Pgdh and $ble^R$ confirmed the arrangement of the latter gene in the correct reading frame.

Transformations of *P. chrysogenum* and *A. chrysogenum* were carried out with the plasmid pALfleo7, the transformants being selected on the basis of their resistance to 30 μg/ml and 10 μg/ml of phleomycin, respectively. The maximum level of phleomycin resistance of the transformants was then established in a solid medium, some being obtained that were capable of growing in the presence of more than 100 μg/ml of phleomycin. In the transformants selected for their phleomycin resistance, analyses were made for the presence of the plasmid by the Southern blot technique and the existence of a transcript corresponding to the $ble^R$ gene by the Northern blot technique, positive results being obtained in both cases. These results confirmed the possibility of expressing heterologous genes in *P. chrysogenum* and *A. chrysogenum* under the control of the Pgdh.

The plasmid pALfleo7 was introduced into *E. coli* with the aim of finding out whether the Pgdh of *P. chrysogenum* was also able to direct the expression of the $ble^R$ gene in *E. coli*. The transformants obtained had the ability to grow in LB with 0.2 μg/ml of phleomycin, the minimum inhibitory concentration of the phleomycin being less than 0.025 μg/ml for *E. coli*. This result confirmed that the Pgdh was expressed in *E. coli*, although less efficiently than in *P. chrysogenum*. A transformant of *E. coli* DH5α with the plasmid pALfleo7 has been deposited in the Spanish Collection of Type Cultures (CECT) with the access number CECT4849. Other plasmids such as pALP784 and pALP785 can be obtained from the deposited plasmid simply by selecting the 2.9 kb Sau3AI-XbaI fragment by hybridization with the promoter of the gdh gene included in pALfleo7, and subcloning it in pBluescript I KS(+) or pUC13, respectively.

1.3. Antisense Expression in P. chrysogenum and A. chrysogenum Under the gdh Promoter The inactivation of gene expression in industrial strains is sometimes necessary for the elimination of undesirable enzyme activities. Owing to the fact that the level of ploidy of many industrial strains makes it difficult in most cases to block expression by direct gene disruption, it is necessary to use systems for inactivation of expression which are independent of the level of ploidy. The development of antisense constructs expressed under the control of strong promoters makes interruption of gene expression possible.

By way of example, the use of the Pgdh to inactivate the expression of the gene which codes for phenylacetate 2-hydroxylase (pahA) in P. chrysogenum is described below. First of all the plasmid pALP873, which carries the Pgdh and the TtrpC fused via a single BamHI site, was constructed. The plasmid pALP873 was digested with BamHI, its ends were filled in with the Klenow fragment of DNA polymerase I and it was ligated with a 1,053 bp cDNA fragment inside the pahA gene obtained from the plasmid pALP555 by EcoRV digestion. The resultant plasmid, called pALP874, was selected because it carried the antisense pahA gene fragment relative to the Pgdh. From this plasmid a 2.5 kb EcoRI-XbaI fragment, carrying the antisense cassette, which was filled in with Klenow and subcloned at the EcoRV site of the plasmid pALfleo7, giving rise to the plasmid pALP888, was purified. This last plasmid is characterized by having a size of 7.9 kb and carrying (I) the antisense cassette of the pahA gene under the control of the Pgdh, (II) the ble$^R$ gene as selection marker in fungi, (III) the chloramphenicol resistance gene as marker in E. coli and (IV) the polylinker of the plasmid pBC KS (+).

Transformations of P. chrysogenum were performed with the plasmid pALP888, the transformants being selected on the basis of their resistance to 30 μg/ml of phleomycin. Of the transformants selected, about 20% showed reduced ability to oxidize phenylacetic acid, with some of them lacking detectable levels of said activity. In these transformants, analyses were made for the presence of the plasmid by the Southern blot technique and the existence of an antisense transcript corresponding to the pahA gene by the Northern blot technique, using an oligonucleotide corresponding to the coding strand as a probe. In both cases positive results were obtained, confirming the possibility of totally or partially blocking undesirable enzyme activities in P. chrysogenum by the use of antisense constructs. These results can be extrapolated to related filamentous fungi and to any enzyme activity, using any of the promoters described in the present patent (Pgdh, Phex, PactPc and PactAc) or any available promoter.

EXAMPLE 2

2.1. Cloning and Characterization of the hex Gene of P. chrysogenum

The presence of a major protein which after purification and characterization was found to be the enzyme β-N-acetylhexosaminidase was determined in the P. chrysogenum mycelium obtained from industrial fermentation under conditions of penicillin G production. The amino acid sequence of the amino terminal end of the purified protein was determined by Edman's degradation method, two different sequences being obtained:

(A) Ala-Pro-Ser-Gly-Ile-His-Asn-Val-Asp-Val-(His)-Val-Val-(Asp)-Asn-(Asp)-Ala-(Asp)-Leu-Gln-Tyr-(Gly) (SEQ ID NO:9)

(B) Val-Gln-Val-Asn-Pro-Leu-Pro-Ala-Pro-(Arg)-(Arg)-Ile-(Thr)-???-(Gly)-(Ser)-(Ser)-(Gly)-(Pro)-(Ile/Thr)-???-(Val)(SEQ ID NO:10)

On the basis of these sequences, and assuming the codon usage trend which exists in a series of P. chrysogenum genes, the following combinations of synthetic oligonucleotides were designed:

5' TCGACGACGTGSACGTCSACGTTGTGGATGCC 3' (SEQ ID NO: 11) (I)

5' CCGTAYTGSAGGTCRGCGTCGTTGTCGACGAC 3' (SEQ ID NO: 12) (II)

5' GGGGCVGGSAGVGGGTTGACYTG 3' (SEQ ID NO: 13)(III)

The hex gene of P. chrysogenum was cloned using the DNA library and the procedures described in Example 1. A total of 11 positive clones were purified and their DNA was then digested with a series of restriction endonucleases and analysed by the Southern blot technique. In this way the hex gene was identified in a 3.2 kb SacI fragment and in a 2.1 kb SalI fragment. Subcloning of the SalI fragment in the plasmid pBC KS(+) (Stratagene) in both orientations generated the plasmids pALP295 and pALP303. The restriction map of the DNA region which includes the hex gene is shown in FIG. 2.

In order to determine the nucleotide sequence of the hex gene, use was made of the above-mentioned plasmids pALP295 and pALP303, as well as pALP319 and pALP461 (both orientations of a 2.8 kb BamHI fragment), pALP388 and pALP389 (both orientations of a 2.4 kb SalI fragment) and pALP377 and pALP378 (both orientations of a 1.2 kb PstI fragment) (FIG. 2). A series of clones were constructed from the said plasmids by the "Erase a base" method (Promega) and then sequenced by the dideoxynucleotide method using the "Sequenase" test kit (USB), in both cases in accordance with the manufacturer's instructions. The 5,240 nucleotide sequence obtained (SEQ ID NO:2) was analysed with the Geneplot program (DNASTAR), confirming the existence of two ORFs with a very marked preferential codon usage pattern. The ATG translation initiation codon of the hex gene was found in position 1,324 and the TGA termination codon in position 3,112. The said ORF lacks introns and codes for a protein of 66,545 Da, with an isoelectric point of 5.34, the 596 amino acid sequence of which (SEQ ID NO:6) has 49.0% identity with the amino acid sequence of the β-N-acetylhexosaminidase enzyme of Candida albicans. In addition, in positions 19–40 and 99–120 the deduced amino acid sequence includes the amino acid sequences determined chemically from the purified enzyme. A protease recognition site (Lys-Arg) appears in the positions immediately adjacent to the amino acid sequence (A) described above (amino acids 97–98).

In the promoter region there are found two pyrimidine-rich zones between positions 1,106–1,128 and 1,182–1,200, a presumed TATA box in position 1,258 (ATAAATA) and a CAAT box in position 1,163.

2.2. Expression of the ble$^R$ gene of S. hindustanus in P. chrysogenum Under the Phex The processes of (I) transformation and selection of P. chrysogenum transformants, (II) analysis of DNA, (III) analysis of RNA and (IV) enzyme measurements were carried out as described in Section 1.2 of Example 1.

In order to express the ble$^R$ gene under the Phex, first of all an NcoI site was constructed above the ATG codon which codes for the initiator methionine of the hex gene. This was carried out by PCR using the following oligonucleotides as primers:

5' CTCCATGGTGATAAGGTGAGTGACGATG 3'(SEQ ID NO:14)

5' GTAAAACGACGGCCAGTG 3' (Primer −20) (SEQ ID NO:15)

The DNA fragment obtained by PCR was subcloned in both orientations in the SmaI site of the plasmid pBC KS (+) (Stratagene), giving rise to pALP427 and pALP428. The inserts of both plasmids were sequenced using the test kits "Erase a base" (Promega) and "Sequenase" (USB), in both cases in accordance with the manufacturer's instructions. In this way it was shown that the Phex obtained lacked mutations and included the NcoI site above the ATG which codes for the initiator methionine of the protein.

pALP427 was the plasmid chosen for carrying out the subcloning of the ble$^R$ gene. The ble$^R$ gene without its promoter region was obtained from the plasmid pUT737 (Mullaney et al. (1985), Mol. Gen. Genet. 199: 37–45) as a 1,100 bp NcoI-ApaI fragment. This fragment was then subcloned in the plasmid pALP427 (carrying the Phex) previously digested with NcoI-ApaI, giving the plasmid pALP480 (FIG. 6). This last plasmid has a size of 5.4 kb, the ble$^R$ gene expressed under the control of the Phex, the terminator of the trpC gene under the ble$^R$ gene, the chloramphenicol resistance gene as marker in E. coli and the polylinker of the plasmid pBC KS (+). The sequencing of the fusion region between Phex and ble$^R$ confirmed the arrangement of the latter gene in the correct reading frame.

Transformations of P. chrysogenum were performed with the plasmid pALP480, the transformants being selected on the basis of their resistance to 30 μg/ml of phleomycin. The maximum level of phleomycin resistance of the transformants was then established in a solid medium, some being obtained that were capable of growing in the presence of more than 100 μg/ml of phleomycin. In the transformants selected for their phleomycin resistance, analyses were made for the presence of the plasmid by the Southern blot technique and the existence of a transcript corresponding to the ble$^R$ gene by the Northern blot technique, positive results being obtained in both cases. These results confirmed the possibility of expressing heterologous genes in P. chrysogenum under the control of the Phex. A transformant of E. coli DH5α with the plasmid pALP480 has been deposited in the Spanish Collection of Type Cultures (CECT) with the access number CECT4852. The plasmids pALP295, pALP319, pALP377 and pALP388 can be obtained from the deposited plasmid simply by selecting the DNA fragments 2.1 kb SalI, 2.8 kb BamHI, 1.2 kb PstI and 2.4 kb SalI, respectively, by hybridization with the promoter of the hex gene included in pALP480, and then subcloning them in pBluescript I KS(+).

2.3. Extracellular Production of Proteins in P. chrysogenum Using the hex Gene The enzyme β-N-acetylhexosaminidase is a protein which is abundantly secreted by P. chrysogenum to the culture medium in industrial fermenters under conditions of penicillin G production. The ability of this enzyme to be secreted makes it possible to use the hex gene for the expression and secretion of homologous or heterologous proteins in P. chrysogenum or related filamentous fungi.

The enzyme has a secretion signal sequence made up of the following amino acids: Met-Lys-Phe-Ala-Ser-Val-Leu-Asn-Val-Leu-Gly-Ala-Leu-Thr-Ala-Ala-Ser-Ala (amino acids 1 to 18 of SEQ ID NO: 6). In general, signal peptides have three conserved structural domains (Takizawa, N. et al. (1994) Recombinant microbes for industrial and agricultural applications, Murooka, Y. and Imanaka, T. (eds), Marcel Dekker, Inc. New York) (I) a positively charged amino terminal region called "n", which usually has from 1 . 5 residues and is needed for the efficient translocation of the protein across the membrane (Met-Lys), (II) a hydrophobic region called "h", made up of 7 to 15 residues (Phe-Ala-Ser-Val-Leu-Asn-Val-Leu) (amino acids 3 to 10 of SEQ ID NO: 6) and (III) a polar region at the carboxyl end, called "c", made up of 3 to 7 residues (Gly-Ala-Leu-Thr-Ala-Ala-Ser-Ala) (amino acids 11 to 18 of SEQ ID NO: 6).

There are two possibilities when it comes to expressing and secreting proteins using the hex gene: (I) fusing the promoter region, including the secretion signal sequence, to the coding region of the gene to be expressed, in a reading frame, and (II) fusing the complete hex gene to the coding region of the gene to be expressed, in a reading frame. Using standard techniques of molecular biology (Sambrook, J. et al. (1989), Molecular Cloning: A Laboratory Manual, Cold Spring Harbor Laboratory, Cold Spring Harbor, N.Y., USA; Ausubel et al. (1987), Current Protocols in Molecular Biology, John Wiley & Sons, New York, USA), any person skilled in the art would be able to use the promoter, including the secretion sequence of the hex gene, or else the complete gene, for the expression and secretion of proteins of interest in P. chrysogenum or related filamentous fungi.

EXAMPLE 3

3.1. Cloning and Characterization of the act Gene of P. chrysogenum

The act gene of P. chrysogenum was cloned using the DNA library and the procedures described in Example 1. In this case the hybridization was performed with an 888 bp NcoI-ClaI fragment originating from the act gene of A. nidulans (Fidel et al. (1988), Gene 70: 283–293). A total of 10 positive clones were purified and their DNA was then digested with a series of restriction endonucleases and analysed by the Southern blot technique. In this way the act gene was identified in a 5.2 kb BamHI fragment, a 4.9 kb EcoRI fragment and a 5.9 kb HindIII fragment. The HindIII fragment was subcloned in both orientations in the plasmid pBluescript I KS(+) (Stratagene), generating the plasmids pALP298 and pALP299. The subcloning of the EcoRI fragment in the plasmid pBluescript I KS(+) (Stratagene) in both orientations generated the plasmids pALP315 and pALP316. The restriction map of the DNA region which includes the act gene is shown in FIG. 3.

In order to determine the nucleotide sequence of the act gene, use was made of the above-mentioned plasmids pALP315 and pALP316. A series of clones were constructed from the said plasmids by the "Erase a base" method (Promega) and then sequenced by the dideoxynucleotide method using the "Sequenase" test kit (USB), in both cases in accordance with the manufacturer's instructions. The 2,994 nucleotide sequence obtained (SEQ ID NO:3) was analysed with the Geneplot program (DNASTAR), confirming the existence of an ORF with a very marked preferential codon usage pattern. The ATG translation initiation codon of the act gene was found in position 494 and the TAA termination codon in position 2,250. Said ORF has 5 introns in positions 501–616, 649–845, 905–1046, 1078–1180 and 1953–2021 and codes for a protein of 41,760 Da, with an isoelectric point of 5.51, the 375 amino acid sequence of which (SEQ ID NO:7) has 98.1% identity with the amino acid sequence of the γ-actin protein of A. nidulans. In the promoter region there are found two extensive pyrimidine-rich zones between positions 356–404 and 418–469, a presumed TATA box in position 259 (TATAAAAAT) and four CAAT boxes in positions 174, 217, 230 and 337.

3.2. Expression of the ble$^R$ Gene in P. chrysogenum Under the PactPc

In order to express the ble$^R$ gene under the PactPc, first of all an NcoI site was constructed above the ATG codon which codes for the initiator methionine of the hex gene. This was carried out by PCR using the following oligonucleotides as primers:

5' CTCCATGGTGACTGATTAAACAAGGG
AC 3' (SEQ ID NO:19)

5' GTAAAACGACGGCCAGTG 3' (Primer -20
) (SEQ ID NO:20)

The DNA fragment obtained by PCR was subcloned in both orientations in the SmaI site of the plasmid pBC KS (+) (Stratagene), giving rise to pALPact1 and pALPact2. The inserts of both plasmids were sequenced using the test kits "Erase a base" (Promega) and "Sequenase" (USB), in both cases in accordance with the manufacturer's instructions. In this way it was shown that the PactPc obtained lacked mutations and included the NcoI site above the ATG. which codes for the initiator methionine of the protein.

pALPact1 was the plasmid chosen for carrying out the subcloning of the ble$^R$ gene. The ble$^R$ gene without its promoter region was obtained from the plasmid pUT737 (Mullaney et al. (1985), Mol. Gen. Genet. 199: 37–45) as a 1,100 bp NcoI-ApaI fragment. This fragment was then subcloned in the plasmid pALPact1 (carrying the PactPc) previously digested with NcoI-ApaI, giving the plasmid pALPfleo1 (FIG. 6). This last plasmid has the ble$^R$ gene expressed under the control of the PactPc, the terminator of the trpC gene under the ble$^R$ gene, the chloramphenicol resistance gene as marker in E. coli and the polylinker of the plasmid pBC KS (+). The sequencing of the fusion region between PactPc and ble$^R$ confirmed the arrangement of the latter gene in the correct reading frame.

Transformations of P. chrysogenum were performed with the plasmid pALPfleo1, the transformants being selected on the basis of their resistance to 30 μg/ml of phleomycin. The maximum level of phleomycin resistance of the transformants was then established in a solid medium, some being obtained that were capable of growing in the presence of more than 100 μg/ml of phleomycin. In the transformants selected for their phleomycin resistance, analyses were made for the presence of the plasmid by the Southern blot technique and the existence of a transcript corresponding to the ble$^R$ gene by the Northern blot technique, positive results being obtained in both cases. These results confirmed the possibility of expressing heterologous genes in P. chrysogenum under the control of the PactPc. A transformant of E. coli DH5α with the plasmid pALP315, which carries the act gene, has been deposited in the Spanish Collection of Type Cultures (CECT) with the access number CECT4851. The plasmid pALP316 can be obtained from the deposited plasmid pALP315 simply by subcloning the pALP315 insert in the EcoRI site of pBluescript I KS(+) in the opposite orientation.

EXAMPLE 4

4.1. Cloning and Characterization of the act Gene of A. chrysogenum

With the aim of cloning the gdh gene of A. chrysogenum, a DNA library was constructed in the phage vector λGEM12, as described in Section 1.1 of Example 1. The phage titre obtained was 50 pfu/μl (a total of 25,000 pfu) in E. coli LE392 and 41 pfu/μl (a total of 20,500 pfu) in E. coli NM539. This meant that about 82% of the phages were carrying an exogenous DNA fragment and that an A. chrysogenum DNA library had been obtained with 99.999% probability. After this series of theoretical verifications had been carried out, E. coli NM539 was infected and the complete DNA library was spread on 3 Petri dishes of 150 mm diameter (about 7,000 pfu/Petri dish), collected in 50 ml of SM plus 2.5 ml of chloroform, and kept at 4° C. In this way a sufficient and representative volume of recombinant phages (2,100 pfu/μl) ready to be plated out at any time was available.

About 20,000 pfu were spread on 2 Petri dishes of 150 mm diameter and then transferred to nitrocellulose filters (BA85, 0.45 μm, Schleicher & Schuell) said filters were hybridized using standard protocols (Molecular Cloning: A Laboratory Manual, Cold Spring Harbor Laboratory, Cold Spring Harbor, N.Y., USA) with an 888 bp NcoI-ClaI fragment corresponding to the act gene of A. nidulans. A total of 5 positive clones were purified and their DNA was then digested with a series of restriction endonucleases and analysed by the Southern blot technique. In this way the act gene was identified in an 8.7 kb HindIII fragment. This fragment was subcloned in both orientations in the plasmid pBluescript I KS(+) (Stratagene), generating the plasmids pALC52 and pALC53. The restriction map of the DNA region which includes the act gene is shown in FIG. 4.

The above-mentioned plasmids pALC52 and pALC53 were used to determine the nucleotide sequence of the act gene. A series of clones were constructed from the said plasmids by the "Erase a base" method (Promega) and then sequenced by the dideoxynucleotide method using the "Sequenase" test kit (USB), in both cases in accordance with the manufacturer's instructions. The 3,240 nucleotide sequence obtained (SEQ ID NO:4) was analysed with the Geneplot program (DNASTAR), confirming the existence of an ORF with a very marked preferential codon usage pattern. The ATG translation initiation codon of the act gene was found in position 787 and the TAA termination codon in position 2,478. Said ORF has 5 introns in positions 794–920, 952–1,123, 1,180–1,289, 1,321–1,410 and 2,183–2,249 and codes for a protein of 41,612 Da, with an isoelectric point of 5.51, the 375 amino acid sequence of which (SEQ ID NO:8) has 98.4% and 98.1% identity with the amino acid sequences of the γ-actin proteins of A. nidulans and P. chrysogenum, respectively. In the promoter region there is found a pyrimidine-rich zone between positions 607–654, a presumed TATA box in position 747 (TTATAAAA) and a CAAT box in position 338.

4.2. Expression of the ble$^R$ Gene in A. chrysogenum Under the PactAc

The plasmid pALCfleo1 (FIG. 6), which includes the ble$^R$ gene expressed under the control of the PactAc, the terminator of the trpC gene under the ble$^R$ gene, the chloramphenicol resistance gene as marker in E. coli and the polylinker of the plasmid pBC KS (+), was constructed for the purpose of expressing the ble$^R$ gene under the control of the PactAc.

The ble$^R$ gene without its promoter region was obtained from the plasmid pUT737 (Mullaney et al. (1985), Mol. Gen. Genet. 199: 37–45) as a 1,100 bp NcoI-ApaI fragment. This fragment was then fused in a reading frame with the PactAc, making use of the fact that the act gene has an NcoI site above the ATG which codes for the initiator methionine of the protein. To this end the ble$^R$ gene was subcloned in the plasmid pALCact1 (carrying the PactAc) previously digested with NcoI-ApaI, giving the plasmid pALCfleo1 (FIG. 6). The sequencing of the fusion region between PactAc and ble$^R$ confirmed the arrangement of the latter gene in the correct reading frame.

Transformations of *A. chrysogenum* were performed with the plasmid pALCfleo1, the transformants being selected on the basis of their resistance to 10 μg/ml of phleomycin. The maximum level of phleomycin resistance of the transformants was then established in a solid medium, some being obtained that were capable of growing in the presence of more than 30 μg/ml of phleomycin. In the transformants selected for their phleomycin resistance, analyses were made for the presence of the plasmid by the Southern blot technique and the existence of a transcript corresponding to the ble$^R$ gene by the Northern blot technique, positive results being obtained in both cases. These results confirmed the possibility of expressing heterologous genes in *A. chrysogenum* under the control of the PactAc. A transformant of *E. coli* DH5α with the plasmid pALC52, which carries the act gene, has been deposited in the Spanish Collection of Type Cultures (CECT) with the access number CECT4850. The plasmid pALC53 can be obtained from the deposited plasmid pALC52 simply by subcloning the pALC52 insert in the HindIII site of pBluescript I KS(+) in the opposite orientation.

The introduction, in actinomycetes, Penicillium, Aspergillus, Acremomium or Saccharomyces, of the inserts present in the deposited plasmids using *E. coli* as host is only a question of technical routine and of choosing the most appropriate vectors for the transformation of said genera or families.

Figure 1:
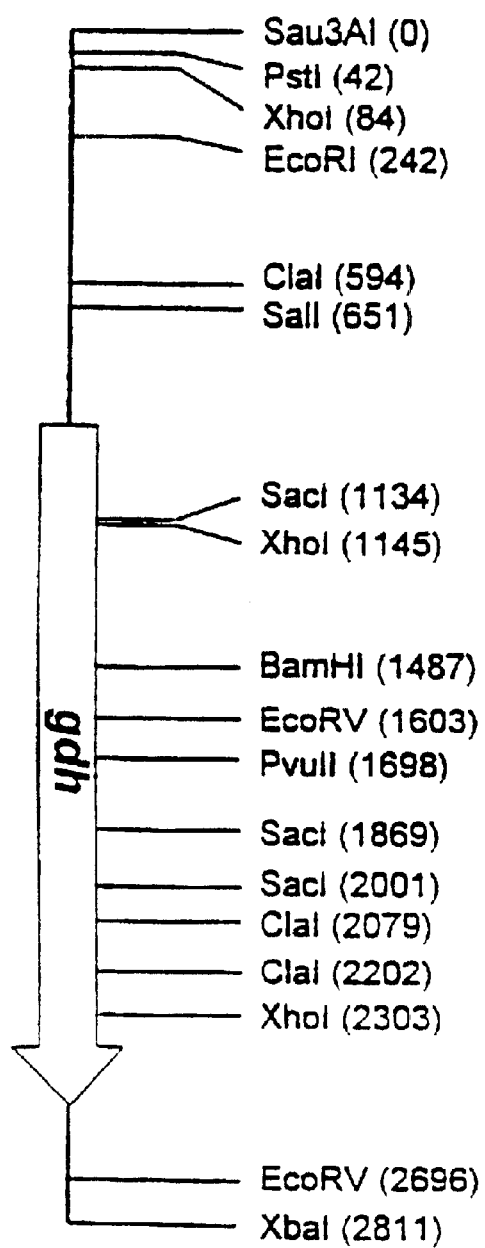
FIG. 1.—Restriction map of the gdh gene of *P. chrysogenum*, which codes for NADP-dependent glutamate dehydrogenase enzyme activity (EC.1.4.1.4).
Figure 2:
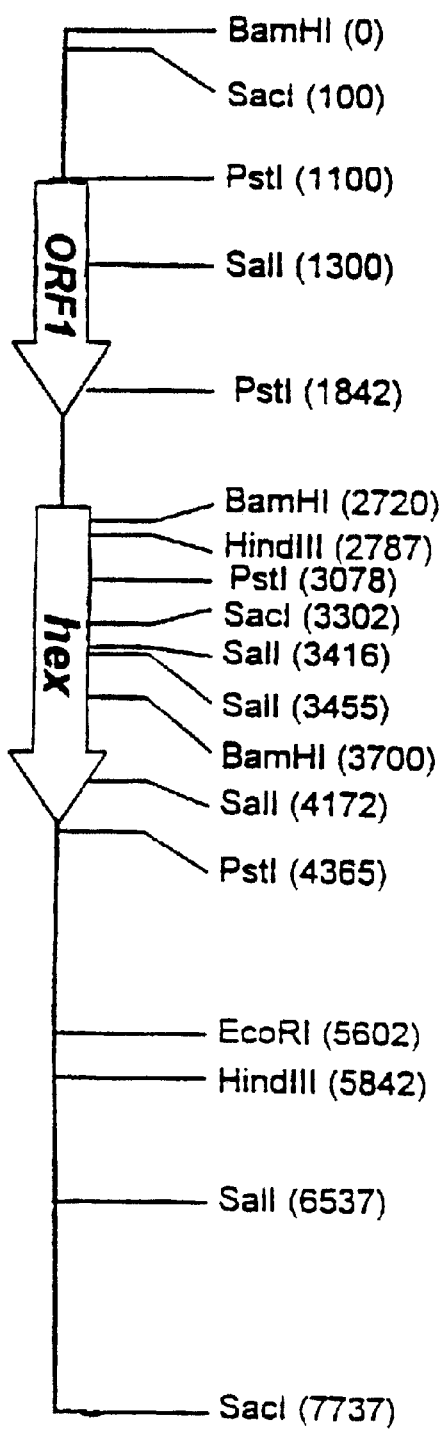
FIG. 2.—Restriction map of the hex gene of *P. chrysogenum*, which codes for β-N-acetylhexosaminidase enzyme activity (EC.3.2.1.52).
Figure 3:
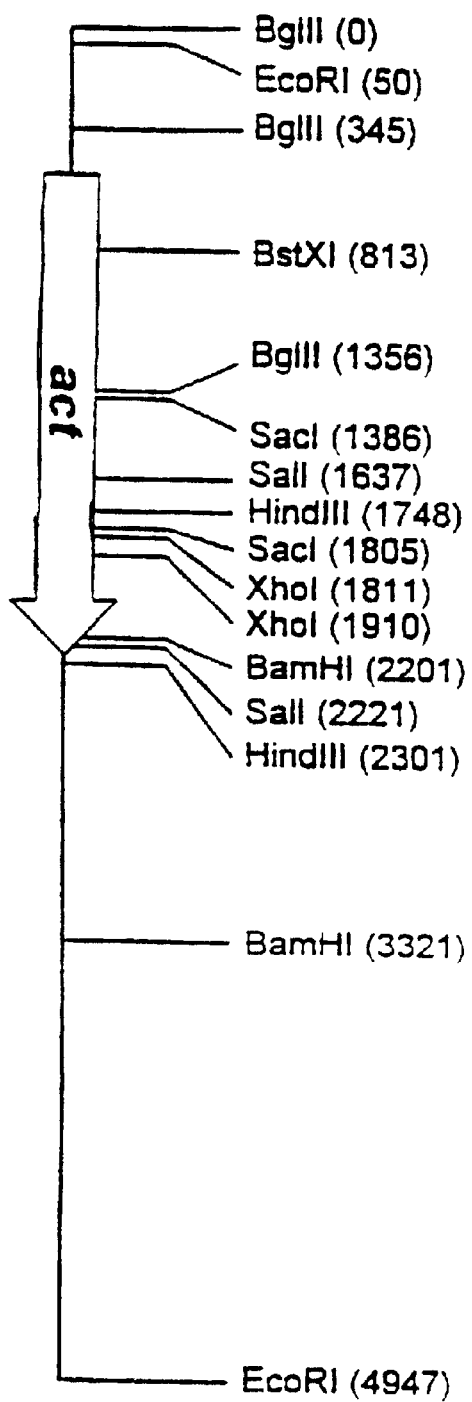
FIG. 3.—Restriction map of the act gene of *P. chrysogenum*, which codes for γ-actin.
Figure 4:
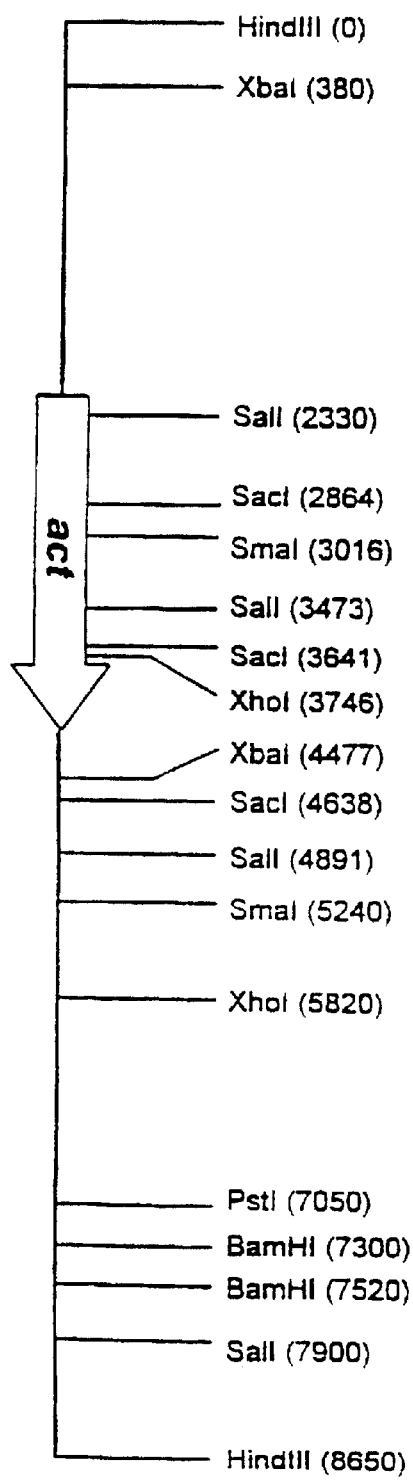
FIG. 4.—Restriction map of the act gene of *A. chrysogenum*, which codes for γ-actin.
Figure 5:
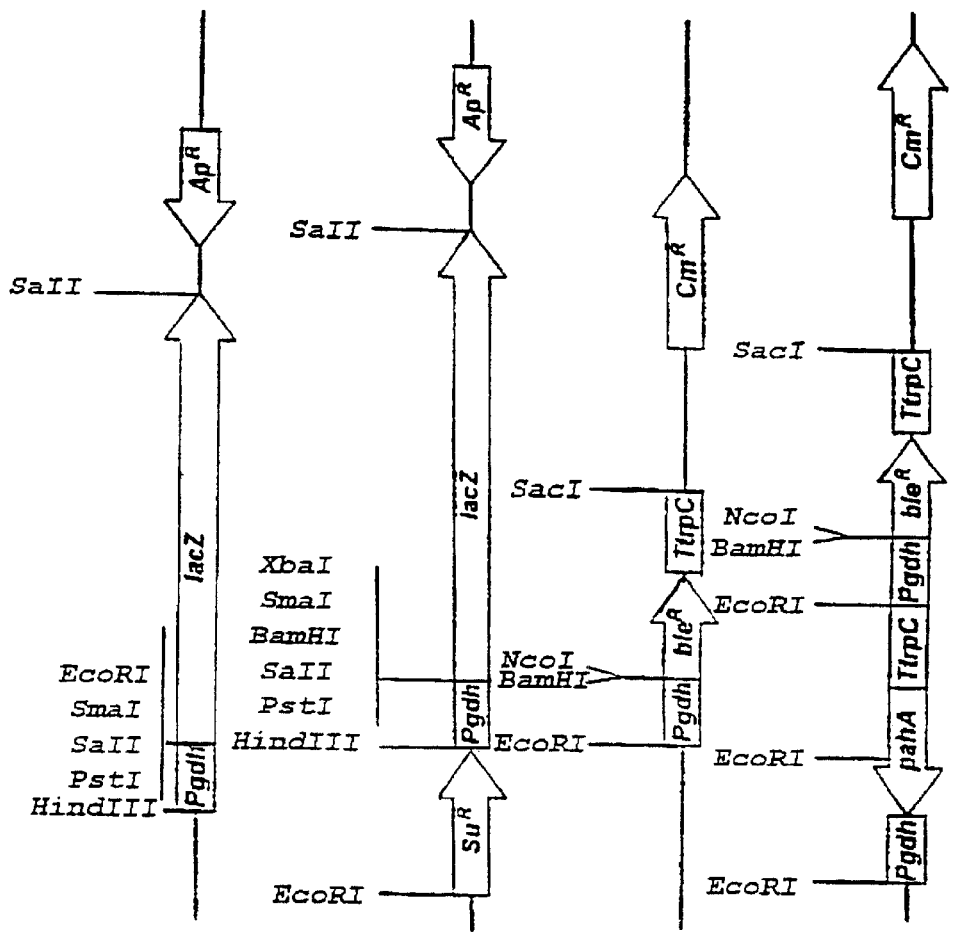
FIG. 5.—Vectors for the expression of the lacZ gene of *E. coli*, the ble$^R$ gene of *S. hindustanus* and the antisense fragment of the pahA gene of *P. chrysogenum* in *P. chrysogenum* and/or *A. chrysogenum* under the promoter Pgdh.
Figure 6:
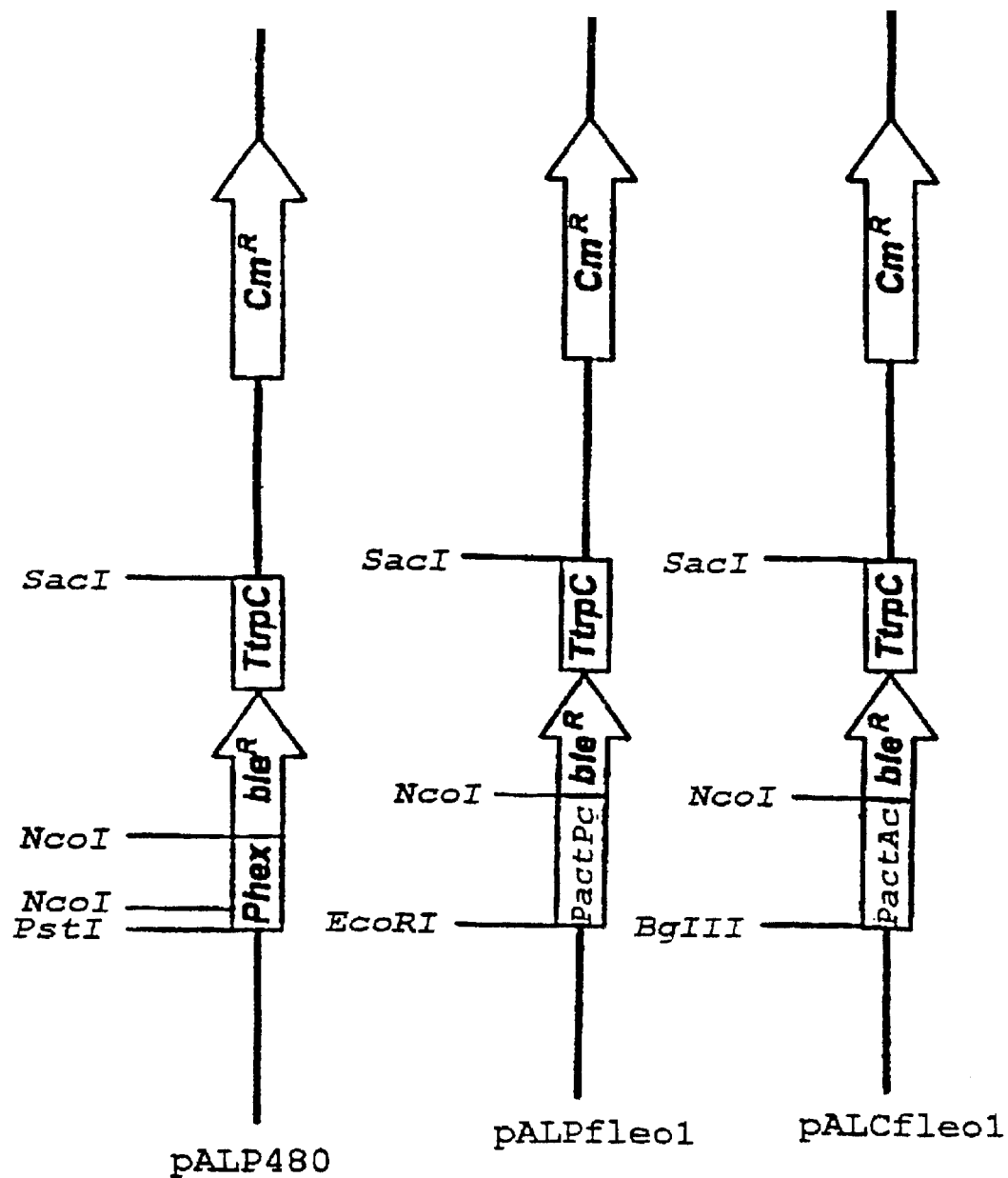
FIG. 6.—Vectors for the expression of the ble$^R$ gene of *S. hindustanus* in *P. chrysogenum* and/or *A. chrysogenum* under the promoters Phex, PactPc, PactAc.

What is claimed is:

1. An isolated DNA comprising the promoter sequence of the hex gene of *P chrysogenum* that is capable of directing expression of DNA downstream of said promoter sequence *P. chrysogenum*.

2. An isolated DNA according to claim 1, comprising 7737 bp of the hex gene of *P. chrysogenum* bounded by a Bam HI restriction site on one side and a Sac I restriction site on the other side.

3. A vector comprising the isolated DNA of claim 1.

4. A process for promoting expression of a coding sequence of interest in a microorganism, said microorganism being one in which the isolated DNA of claim 1 is capable of directing expression of DNA downstream of the isolated DNA, said process comprising:
   (a) providing a DNA construct comprising the isolated DNA operably linked to the coding sequence of interest; and
   (b) transforming the microorganism with the DNA construct to cause expression of the coding sequence of interest.

5. A process to block expression of a gene of interest in a microorganism, said microorganism being one in which the isolated DNA of claim 1 is capable of directing expression of DNA downstream of the isolated DNA, said process comprising:
   (a) providing a DNA construct comprising the isolated DNA with an antisense polynucleotide operably linked thereto, said antisense polynucleotide being sufficiently complementary to the gene of interest to block expression of the gene of interest when the antisense polynucleotide is expressed in the microorganism;
   (b) transforming the microorganism with the DNA construct to cause expression of the antisense polynucleotide whereby to block expression of the gene of interest.

6. A vector comprising the isolated DNA of claim 2.

7. A vector according to claim 3, comprising a plasmid selected from the group consisting of pALP295, pALP319, pALP388, pALP377, pALP480.

8. A process according to claim 4, wherein the microorganism is selected from the group consisting of *Penicillium chrysogenum, Aspergillus nidulans* and *Acremonium chrysogenum*.

9. A process according to claim 4, wherein the coding sequence is not naturally associated with said isolated DNA.

10. A process according to claim 5, wherein the microorganism is selected from the group consisting of *Penicillium chrysogenum, Aspergillus nidulans* and *Acremonium chrysogenum*.

11. A process according to claim 5, wherein the gene of interest is not naturally associated with said isolated DNA.

12. An isolated DNA encoding a β-N-acetylhexosaminidase enzyme of *P. chrysogenum*.

13. An isolated DNA according to claim 12, wherein the enzyme comprises SEQ ID NO:6.

14. A vector comprising the isolated DNA of claim 12.

15. A vector comprising the isolated DNA of claim 13.

16. An isolated DNA comprising SEQ ID NO: 2 that encodes a β-N-acetylhexosaminidase enzyme.

17. An isolated DNA according to claim 16, wherein the isolated DNA encodes the amino acid sequence of SEQ ID NO:6.

18. A vector comprising the isolated DNA of claim 16.

19. A vector comprising the isolated DNA of claim 17.

20. A process for transforming a microorganism comprising:
   (a) providing the vector of claim 19, with the isolated DNA operably linked to a regulatory sequence capable of directing expression of said isolated DNA in said microorganism; and
   (b) transforming the microorganism with the vector to cause expression of the isolated DNA.

21. A process according to claim 20, wherein the microorganism is
(i) a prokaryote selected from the group consisting *E coli* and an actinomycete or
(ii) a eukaryote selected from the genus consisting of Penicillium, Aspergillus, Acremonium and Saccharomyces.

22. A process for transforming a microorganism comprising:
(a) providing the vector of claim 18, with the isolated DNA operably linked to a regulatory sequence capable of directing expression of said isolated DNA in said microorganism; and
(b) transforming the microorganism with the vector to cause expression of the isolated DNA.

23. A process according to claim 22, wherein the microorganism is
(i) a prokaryote selected from the group consisting *E. coli* and an actinomycete or
(ii) a eukaryote selected from the genus consisting of Penicillium, Aspergillus, Acremonium and Saccharomyces.

24. A purified protein comprising the amino acid sequence of SEQ ID NO:6.

25. A process for the expression and extracellular secretion of a protein in a microorganism, said protein being encoded by a DNA molecule, said process comprising:
a) providing an isolated DNA comprising SEQ ID NO: 2 that directs expression and extracellular secretion of a protein encoded by a polynucleotide operably linked to the isolated DNA;
b) fusing the DNA molecule to the isolated DNA to form a construct in which the DNA molecule is operably linked to the isolated DNA; and
c) transforming the microorganism with the DNA construct to cause expression of the protein in the microorganism and extracellular secretion of the protein.

26. A process according to claim 25, wherein the microorganism is selected from the group consisting of *Penicillium chrysogenum, Aspergillus nidulans* and *Acremonium chrysogenum.*

27. A process according to claim 25, wherein the DNA molecule is not naturally associated with said isolated DNA.

* * * * *

```
                         SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
          (A) LENGTH: 2816 base pairs
          (B) TYPE: nucleotides
          (C) STRANDEDNESS: double
          (D) TOPOLOGY: linear (ii) MOLECULE TYPE: genomic DNA (iii) HYPOTHETICAL: NO (iv) ANTI-SENSE: NO (vi) ORIGINAL SOURCE:
          (A) ORGANISM: Penicillim chrysogenum (vii) IMMEDIATE SOURCE:
          (B) CLONE: plasmids pALP784 and pALP 785

(ix) FEATURE:
          (A) NAME/KEY: coding sequence
          (B) LOCATION: join (922...970, 1131...1261, 1319   2521)

(ix) FEATURE:
          (A) NAME/KEY: intron
          (B) LOCATION: 971...1130

(ix) FEATURE:
          (A) NAME/KEY: intron
          (B) LOCATION: 1262...1318

(ix) FEATURE:
          (D) OTHER INFORMATION: gdh gene
```

(xi) SEQUENCE DESCRIPTION: SEQ ID NO: 1

```
GATCGCCGTT TATGGGATAG TGGGCACGTG ACAGAGCCTG CAGCCGAGTC AAATTGCCGA      60

AGTTGGCAGT TGGTGGCGGA GAACTCGAGA TTTTATTTGC GTTTATTTCG TTTATTTCGA     120

TTTTAGTTTT CCTATTTTTC CTATTTTGGT TGATTCCATC CAACTTTATA GGATACTACT     180

TCATAATAGG TCGATCATAG TACAAGCACC AACTCGTCGC ATCATGCATT TTCTGGGGTT     240

CGAATTCTTT ACTTAGAGTA AGGTTTCTCT CAGCCTCCTA ATAAACTACC TAGGTAGGTT     300

AAATTTACTT TTTAACATTT TATTTATTCA GAAGATTGTC GGAGAGGACC GATCCGAAGG     360

ACACGAATTG AACACGGAAG GGATATTAGG GACAAGGAAG ATTTAGGGAT AAAAAAACGA     420

GCTGTGATTG ATGGGAAGGT TAAAGTGTAG TAATGAAGGT GATGGGACCA AAAGGAGTGG     480

GAGAGATAAG CCAAATTCTG TGCAAATTCT GTGACCTTAA ACCATAAGAT AACATTGTTC     540

GGGCCCCGAA CTTCGGACGT TCTTCCCACG GAAAGGCAAA TCATTGGGTT TCATCGATTC     600

TCTTGGATCT TTATCCTAAT TCCCCGTGCA ACCTGGTCTT GGGGATTATT GTCGACTTGT     660

AGGCGCATTA ACCCATCTCC CGTCTTCCCT CCAATCAATC CCGGATTCTC TCGTCCGACT     720

CCGGCTTCGA CTCTCTCTCT CTCCACATCT CTATATAATT GTACACTCCC CCATCCCATT     780

CTTTTCTTCT CTTCTCATCT ACTCTCTTGA ATCTCAATTG TCTTAATACT CTCTCTGCTC     840

TTGTCTTTAT TTATAATTTA TTAGATCACT GCTTAGCATT GATCTACTTA CCTAAAAGCA     900

GAGTTAACAG TACCGGCCGA A ATG ATG CAA AAC CTT CCC TTC GAG CCT GAG         951
                        Met Met Gln Asn Leu Pro Phe Glu Pro Glu
                         1               5                  10

TTC GAG CAG GCC TAC AAG G GTATGTCTCT TTTAATTTTT CCCTTTCTTA TTTCAA     1006
Phe Glu Gln Ala Tyr Lys
             15

TTCCATATCG TCCATATCAC ACACTATTTC CCGACTCAAT TCCTTTACCC ATCGGCATCT     1066

TCCCGGCCTT TGGCTCCACC GGGGGCATAA TTTCGGGGTG ACTCAGCTAA CAATCCCGAA     1126

ACAG  AG CTC GCC TCC ACT CTC GAG AAC TCC ACT CTT TTC CAG AAG AAG      1174
      Glu Leu Ala Ser Thr Leu Glu Asn Ser Thr Leu Phe Gln Lys Lys
              20                  25                  30

CCC GAG TAC CGC AAG GCT CTT CAG GTC GTC TCT GTC CCC GAG CGT GTT      1222
Pro Glu Tyr Arg Lys Ala Leu Gln Val Val Ser Val Pro Glu Arg Val
             35                  40                  45

ATT CAG TTC CGT GTT GTC TGG GAA GAT GAC AAA GGC CAG GTAAGACCTT       1271
Ile Gln Phe Arg Val Val Trp Glu Asp Asp Lys Gly Gln
         50                  55                  60

TCTTTTTGAA AATGTCTAAT TAATTGCCAC ATGCTAATTC CGTTCAG GTC CAA ATC     1327
                                                     Val Gln Ile

AAC CGT GGA TAC CGT GTC CAG TTC AAC TCC GCT CTT GGC CCC TAC AAG     1375
Asn Arg Gly Tyr Arg Val Gln Phe Asn Ser Ala Leu Gly Pro Tyr Lys
     65                  70                  75

GGT GGC CTC CGG TTC CAC CCC ACG GTG AAC CTT TCC ATC CTC AAG TTC     1423
Gly Gly Leu Arg Phe His Pro Thr Val Asn Leu Ser Ile Leu Lys Phe
 80                  85                  90                  95

CTC GGT TTC GAG CAG ATC TTC AAG AAT GCC CTC ACC GGC CTG AAC ATG     1471
Leu Gly Phe Glu Gln Ile Phe Lys Asn Ala Leu Thr Gly Leu Asn Met
                100                 105                 110

GGC GGT GGT AAG GGT GGA TCC GAC TTC GAC CCC AAG GGC AAG ACC GAT     1519
Gly Gly Gly Lys Gly Gly Ser Asp Phe Asp Pro Lys Gly Lys Thr Asp
            115                 120                 125

AAC GAG ATC CGC CGC TTC TGT GTC TCC TTC ATG ACC GAG CTG TGC AAG     1567
Asn Glu Ile Arg Arg Phe Cys Val Ser Phe Met Thr Glu Leu Cys Lys
        130                 135                 140
```

```
CAC ATC GGT GCC GAC ACC GAT GTT CCC GCC GGT GAT ATC GGT GTG ACC         1615
His Ile Gly Ala Asp Thr Asp Val Pro Ala Gly Asp Ile Gly Val Thr
    145                 150                 155

GGC CGC GAG GTT GGT TTC ATG TTC GGC CAG TAC AAG AAG ATC CGC AAC         1663
Gly Arg Glu Val Gly Phe Met Phe Gly Gln Tyr Lys Lys Ile Arg Asn
160                 165                 170                 175

CAG TGG GAG GGT GTC CTC ACC GGT AAG GGT GGC AGC TGG GGT GGT TCC         1711
Gln Trp Glu Gly Val Leu Thr Gly Lys Gly Gly Ser Trp Gly Gly Ser
                180                 185                 190

CTC ATC CGC CCC GAG GCC ACC GGC TAC GGT GTC GTC TAC TAC GTC GAG         1759
Leu Ile Arg Pro Glu Ala Thr Gly Tyr Gly Val Val Tyr Tyr Val Glu
        195                 200                 205

CAC ATG ATC CAG CAC GCC TCC GGC GGC AAG GAA TCC TTC GCT GGT AAG         1807
His Met Ile Gln His Ala Ser Gly Gly Lys Glu Ser Phe Ala Gly Lys
            210                 215                 220

CGC GTC GCC ATC TCC GGT TCC GGA AAC GTC GCC CAG TAC GCC GCT CTC         1855
Arg Val Ala Ile Ser Gly Ser Gly Asn Val Ala Gln Tyr Ala Ala Leu
    225                 230                 235

AAG GTC ATC GAG CTC GGT GGC TCC GTC ATC TCC CTC TCC GAC TCC CAG         1903
Lys Val Ile Glu Leu Gly Gly Ser Val Ile Ser Leu Ser Asp Ser Gln
240                 245                 250                 255

GGT GCT CTC GTC CTG AAC GGC GAG GAG GGC TCC TTC ACC GCT GAG GAG         1951
Gly Ala Leu Val Leu Asn Gly Glu Glu Gly Ser Phe Thr Ala Glu Glu
                260                 265                 270

ATC AAC ACC ATC GCT GAG ATC AAG GTC CAG CGC AAG CAG ATC GCC GAG         1999
Ile Asn Thr Ile Ala Glu Ile Lys Val Gln Arg Lys Gln Ile Ala Glu
        275                 280                 285

CTC GCT ACC CAG GAC GCC TTC AGC TCC AAG TTC AAG TAC ATC CCC GGT         2047
Leu Ala Thr Gln Asp Ala Phe Ser Ser Lys Phe Lys Tyr Ile Pro Gly
            290                 295                 300

GCC CGC CCC TGG ACC AAC ATC GCC GGC CGC ATC GAT GTC GCT CTC CCC         2095
Ala Arg Pro Trp Thr Asn Ile Ala Gly Arg Ile Asp Val Ala Leu Pro
    305                 310                 315

TCC GCC ACC CAG AAC GAG GTC TCC GGC GAT GAG GCC AAG GCT CTC ATC         2143
Ser Ala Thr Gln Asn Glu Val Ser Gly Asp Glu Ala Lys Ala Leu Ile
320                 325                 330                 335

GCC GCT GGC TGC AAG TTC ATC GCT GAG GGC TCC AAC ATG GGT TCC ACC         2191
Ala Ala Gly Cys Lys Phe Ile Ala Glu Gly Ser Asn Met Gly Ser Thr
                340                 345                 350

CAG GAG GCT ATC GAT GTC TTC GAG GCC CAC CGT GAT GCC AAC CCT GGT         2239
Gln Glu Ala Ile Asp Val Phe Glu Ala His Arg Asp Ala Asn Pro Gly
        355                 360                 365

GCC GCT GCC ATC TGG TAC GCC CCT GGT AAG GCC GCC AAC GCT GGT GGT         2287
Ala Ala Ala Ile Trp Tyr Ala Pro Gly Lys Ala Ala Asn Ala Gly Gly
            370                 375                 380

GTT GCC GTC TCT GGT CTC GAG ATG GCC CAG AAC TCT GCC CGT GTC AAC         2335
Val Ala Val Ser Gly Leu Glu Met Ala Gln Asn Ser Ala Arg Val Asn
    385                 390                 395

TGG TCC CGT GAG GAG GTT GAC TCC CGT CTT AAG AAG ATT ATG GAG GAC         2383
Trp Ser Arg Glu Glu Val Asp Ser Arg Leu Lys Lys Ile Met Glu Asp
400                 405                 410                 415

TGC TTC AAC AAC GGT CTC TCT ACT GCT AAG GAG TAT GTC ACC CCT GCT         2431
Cys Phe Asn Asn Gly Leu Ser Thr Ala Lys Glu Tyr Val Thr Pro Ala
                420                 425                 430

GAG GGT GTT CTT CCT TCC CTC GTG GCT GGC TCC AAC ATT GCT GGT TTC         2479
Glu Gly Val Leu Pro Ser Leu Val Ala Gly Ser Asn Ile Ala Gly Phe
        435                 440                 445

ACC AAG GTC GCT GAG GCC ATG AAG GAG CAC GGT GAC TGG TGG TAAATTA        2531
Thr Lys Val Ala Glu Ala Met Lys Glu His Gly Asp Trp Trp
    450                 455                 460
```

| | |
|---|---:|
| GCATCCCCAT TTATTCTGGG AGGTGTTCTG TGACGATTTC TGTCCTCTCT TAAGGAGAGG | 2591 |
| CAGCTTTGAT GCATTTTCTT TTCATTTAAA TAGCTTTTTA CCCTTTTTGT CAAGCGGGTT | 2651 |
| ACGGATAGAG GCGCTTGGTT TTCTCCACTG TTGCATTCGA TTGATATCCC CACTTGAGCA | 2711 |
| CCGCTGTTTG TTTTGGTTCT GCACTTGGGA CTGTCATGAT GATAATGAGA TACAATGAAT | 2771 |
| AACTTAAAAA TAATTGTGTG GTCTCGTAAA GTTGTAAACT CTAGA | 2816 |

(2) INFORMATION FOR SEQ ID NO: 2

(i) SEQUENCE CHARACTERISTICS:
        (A) LENGTH: 5240 base pairs
        (B) TYPE: nucleotides
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Penicillum chrysogenum (vii) IMMEDIATE SOURCE:
        (B) CLONE: plasmids pALP295 and pALP 388

(ix) FEATURE:
        (A) NAME/KEY: coding sequence
        (B) LOCATION: 1324    3111

(ix) FEATURE:
        (D) OTHER INFORMATION: hex gene (xi) SEQUENCE DESCRIPTION: SEQ ID NO: 2

| | |
|---|---:|
| GTCGACCTCG CAACAGTCGA GAAGCACGCC GCCTATCTCG CCCGCAGCGG GGTAACCGGC | 60 |
| CTAGTAACCC AGGGTAGCAA TGGCGAAGCC GTCCACCTAG ACCGGGAAGA ACGCAAGGCC | 120 |
| ATCACAGCCG CCACACGCCG CGCCGTGGAC GCAGCCGGCT ACAGCAACAT GCCGGTGATT | 180 |
| GCCGGCTGTG GCGCCGCCTC AACCCGTGAG ACCATCCAAT TCTGCCAGGA CTCCGGTGCA | 240 |
| GCAGGCGCCG ACGCTGTCCT CGTGCTCCCA CCCAGCTACT ACAAGTCCCT CGTGAGCACC | 300 |
| GAGTCCATGC ACGCCCACTT CCGGGCTGTG GCCGATGCCT CGCCCGTCCC TGTCCTCATC | 360 |
| TACAACTTCC CCGGCGTGCA GTCCGGCCTC GATCTCAGCT CAGATGATAT CTTAACTCTC | 420 |
| GCAGAACACC CCAATATCAT CGGCTGTAAG CTCACGTGCG GCAACACGGG TAAGTTGGCT | 480 |
| CGTGTTGCGG CGGCCAAGCC GGATTTCTTG ACTTTTGGTG GCTCGGCCGA TTTCACGCTG | 540 |
| CAGACGCTGG TTGTTGGTGG GGCGGGGATT ATCGGTGGCG TGGCTAACAT GATTCCTCGC | 600 |
| TCGTGTGTGC GTCTGATGGA GTTGTATCGT GCTGGGAAGG TTCAGGAGGC GCAGAAGGTG | 660 |
| CAGGCTATTG TTGCGCGCGC TGACTGGGCT GCTATCCATG GTGGCTTTAT CGCTGTTAAG | 720 |
| ACGGGCCTCC AAGCCTACCA CGGTTACGGT GGTCTTCCTC GGCGGCCTTG TGTCGTGCCT | 780 |
| TCTGCTAAGG ATGCGGCAGC CATTCAGGAG GAGTTCCGGG AGGGAATGGA GCTGGAGAAG | 840 |
| TCGTTGGAGT CCTAATGGAT ATAGTAGATT AAATCATGAT TACCAGAGAT CCCATGTGGA | 900 |
| GATTTCTATT CCTTTCCAGG GGTTTTCCAG GGGTTTTCCA GATGTTTTCC AGGTGTTTTC | 960 |
| CAAATGTTTC AGGTTGCTTC ATAGATCGAC AGACCGGTGT GACTGTGTCA TTTGCCAGTA | 1020 |
| GATCCGGAGA TCCCGTAGCT TTCCCCCTCT TTATCTTTTA ATATTTGTTG TTATATGGGA | 1080 |
| GTTCAAGTTG CATGTAGAGG TTGCACTCTC TCTCTCTCTC TTTCCCTTGA ATTATTTGAG | 1140 |

```
TCCAAGGTGT GTTAGTTGTA TGCAATGTAA CTAGGGAGCT GTTTGTTTTT CCCCTTCCCC    1200

AGGGTTGCAT CCTGGGCCAT TCCCCATTCC GATGAAAGAT CGACAATGCA GCTAAACATA    1260

AATAGTTCTG GTTATCTCCT GGCCACAGTT TCTCTACTTT TCATCGTCAC TCACCTTATC    1320

AAC ATG AAG TTC GCC TCG GTG TTG AAT GTG CTC GGG GCC CTG ACG GCT      1368
    Met Lys Phe Ala Ser Val Leu Asn Val Leu Gly Ala Leu Thr Ala
    1               5                   10                  15

GCG TCC GCC GTC CAA GTG AAT CCA CTT CCC GCC CCC CGT AAC ATC ACC      1416
Ala Ser Ala Val Gln Val Asn Pro Leu Pro Ala Pro Arg Asn Ile Thr
                20                  25                  30

TGG GGA TCC TCC GGT CCA ATC CAA GTC AAC AAC TTG AAT CTC AAC GGT      1464
Trp Gly Ser Ser Gly Pro Ile Gln Val Asn Asn Leu Asn Leu Asn Gly
            35                  40                  45

CCT CAC TCC CCT TTG CTC ACT CAA GCT TGG GAG CGA GCA TGG GAA ACC      1512
Pro His Ser Pro Leu Leu Thr Gln Ala Trp Glu Arg Ala Trp Glu Thr
        50                  55                  60

ATC ACC ACC CTG CAA TGG GTT CCT GCT GCT GTT GAA TCC CCA ATC GCC      1560
Ile Thr Thr Leu Gln Trp Val Pro Ala Ala Val Glu Ser Pro Ile Ala
    65                  70                  75

TCC TAT CCG GCC TTC CCC ACC TCG ACC CCT GTC TCC TCT GCC CCC AAG      1608
Ser Tyr Pro Ala Phe Pro Thr Ser Thr Pro Val Ser Ser Ala Pro Lys
80              85                  90                  95

GCC AAA CGC GCG CCC TCC GGA ATC CAT AAC GTC GAT GTT CAT GTG GTG      1656
Ala Lys Arg Ala Pro Ser Gly Ile His Asn Val Asp Val His Val Val
                100                 105                 110

GAC AAC GAT GCC GAT CTC CAA TAC GGT GTG GAT GAA TCC TAT ACA CTG      1704
Asp Asn Asp Ala Asp Leu Gln Tyr Gly Val Asp Glu Ser Tyr Thr Leu
            115                 120                 125

GTA GTG AGC GAT GGT GGC ATC AGG ATC AAT TCT CAG ACG GTC TGG GGT      1752
Val Val Ser Asp Gly Gly Ile Arg Ile Asn Ser Gln Thr Val Trp Gly
        130                 135                 140

GTG TTG CAG GCA TTC ACC ACC CTG CAG CAG ATT ATC ATC TCG GAT GGG      1800
Val Leu Gln Ala Phe Thr Thr Leu Gln Gln Ile Ile Ile Ser Asp Gly
    145                 150                 155

AAG GGC GGT TTG ATC ATT GAA CAG CCC GTC AAG ATC AAG GAT GCC CCG      1848
Lys Gly Gly Leu Ile Ile Glu Gln Pro Val Lys Ile Lys Asp Ala Pro
160                 165                 170                 175

CTG TAC CCC CAT CGT GGT ATC ATG ATA GAC ACC GGG CGC AAC TTC ATT      1896
Leu Tyr Pro His Arg Gly Ile Met Ile Asp Thr Gly Arg Asn Phe Ile
                180                 185                 190

ACC GTT CGC AAG CTC CTT GAG CAG ATC GAC GGT ATG GCC CTG TCC AAG      1944
Thr Val Arg Lys Leu Leu Glu Gln Ile Asp Gly Met Ala Leu Ser Lys
            195                 200                 205

CTC AAT GTT CTC CAC TGG CAC TTG GAC GAT TCT CAG TCG TGG CCC ATG      1992
Leu Asn Val Leu His Trp His Leu Asp Asp Ser Gln Ser Trp Pro Met
        210                 215                 220

CAG ATG AGC TCC TAC CCG GAG ATG ACC AAA GAT GCT TAC TCG CCT CGC      2040
Gln Met Ser Ser Tyr Pro Glu Met Thr Lys Asp Ala Tyr Ser Pro Arg
    225                 230                 235

GAA ATC TAC ACC GAG CAC GAC ATG CGC CGC GTG ATT GCC TAC GCA CGC      2088
Glu Ile Tyr Thr Glu His Asp Met Arg Arg Val Ile Ala Tyr Ala Arg
240                 245                 250                 255

GCG CGA GGT GTC CGC GTC ATC CCC GAG GTC GAC ATG CCC GCC CAC TCA      2136
Ala Arg Gly Val Arg Val Ile Pro Glu Val Asp Met Pro Ala His Ser
                260                 265                 270

GCC TCC GGC TGG CAG CAG GTC GAC CCG GAG ATC GTG GCA TGT GCC GAA      2184
Ala Ser Gly Trp Gln Gln Val Asp Pro Glu Ile Val Ala Cys Ala Glu
            275                 280                 285

TCC TGG TGG TCG AAC GAC GTT TGG GCG GAG CAC ACC GCC GTC CAG CCG      2232
```

```
Ser Trp Trp Ser Asn Asp Val Trp Ala Glu His Thr Ala Val Gln Pro
        290                 295                 300

AAC CCT GGC CAG CTC GAC ATT ATC TAC CCC AAG ACC TAC GAA GTT GTC         2280
Asn Pro Gly Gln Leu Asp Ile Ile Tyr Pro Lys Thr Tyr Glu Val Val
305                 310                 315

AAC AAT GTC TAC CAG GAA TTG TCT CGC ATC TTC AGC GAC AAC TTG TTC         2328
Asn Asn Val Tyr Gln Glu Leu Ser Arg Ile Phe Ser Asp Asn Leu Phe
320                 325                 330                 335

CAC GTT GGT GCA GAC GAG ATC CAG CCC AAC TGC TAC AAC TAC AGC ACC         2376
His Val Gly Ala Asp Glu Ile Gln Pro Asn Cys Tyr Asn Tyr Ser Thr
            340                 345                 350

CAT ATC ACT AAG TGG TTT GCC GAG GAT CCC TCG CGC ACC TAC AAC GAC         2424
His Ile Thr Lys Trp Phe Ala Glu Asp Pro Ser Arg Thr Tyr Asn Asp
            355                 360                 365

CTT GCG CAG TAC TGG GTT GAC CAT TCC ATG CCC ATC TTC CGT AGT GTC         2472
Leu Ala Gln Tyr Trp Val Asp His Ser Met Pro Ile Phe Arg Ser Val
            370                 375                 380

GGC GAC CAC CGC CGT CTT ATG ATG TGG GAG GAC ATA GCT ATC GCG ACT         2520
Gly Asp His Arg Arg Leu Met Met Trp Glu Asp Ile Ala Ile Ala Thr
385                 390                 395

GAA AGC GCC CAC GAC GTG CCC AAA GAC GTC ATC ATG CAG ACC TGG AAC         2568
Glu Ser Ala His Asp Val Pro Lys Asp Val Ile Met Gln Thr Trp Asn
400                 405                 410                 415

AGC GGC GAG GGT GAG GGT AAC ATC AAG AAA CTC ACC TCC GCC GGC TAC         2616
Ser Gly Glu Gly Glu Gly Asn Ile Lys Lys Leu Thr Ser Ala Gly Tyr
            420                 425                 430

GAC GTT GTC GTT TCG ACC TCC GAT TTC CTC TAC CTC GAC TGC GGG CGC         2664
Asp Val Val Val Ser Thr Ser Asp Phe Leu Tyr Leu Asp Cys Gly Arg
            435                 440                 445

GGC GGC TAT GTC ACC AAC GAC GCC CGC TAC AAC GTG CAG AGC AAC ACC         2712
Gly Gly Tyr Val Thr Asn Asp Ala Arg Tyr Asn Val Gln Ser Asn Thr
            450                 455                 460

GAC GGC GGA GTG AAC TTC AAC TAC GGC GGC GAC GGT GGC TCC TGG TGC         2760
Asp Gly Gly Val Asn Phe Asn Tyr Gly Gly Asp Gly Gly Ser Trp Cys
465                 470                 475

GCC CCC TAC AAG ACC TGG CAG CGC ATC TAC GAC TAC GAC TTC CTC ACG         2808
Ala Pro Tyr Lys Thr Trp Gln Arg Ile Tyr Asp Tyr Asp Phe Leu Thr
480                 485                 490                 495

AAT CTC ACT TCC TCC GAA GCG AAG CAC ATT ATC GGC GCC GAG GCT CCT         2856
Asn Leu Thr Ser Ser Glu Ala Lys His Ile Ile Gly Ala Glu Ala Pro
            500                 505                 510

TTG TGG TCG GAG CAG GTC GAC GAT GTG ACC GTC TCC AGC GTG TTC TGG         2904
Leu Trp Ser Glu Gln Val Asp Asp Val Thr Val Ser Ser Val Phe Trp
            515                 520                 525

CCT CGC GCT GCT GCT CTG GGT GAG CTT GTC TGG TCT GGT AAC CGT GAC         2952
Pro Arg Ala Ala Ala Leu Gly Glu Leu Val Trp Ser Gly Asn Arg Asp
            530                 535                 540

GCT GCG GGT AGA AAG CGT ACC ACC AGC TTT ACT CAG CGT ATT CTG AAC         3000
Ala Ala Gly Arg Lys Arg Thr Thr Ser Phe Thr Gln Arg Ile Leu Asn
545                 550                 555

TTC CGT GAA TAC CTC GTT GCC AAT GGT GTG ATG GCT ACT GCT CTT GTG         3048
Phe Arg Glu Tyr Leu Val Ala Asn Gly Val Met Ala Thr Ala Leu Val
560                 565                 570                 575

CCG AAG TAT TGT CTG CAG CAC CCT CAT GCT TGC GAC CTC TAT AAA AAC         3096
Pro Lys Tyr Cys Leu Gln His Pro His Ala Cys Asp Leu Tyr Lys Asn
            580                 585                 590

CAG ACT GTA ATG TCT TGATTGTGGT TAAGCTGGAC TGCTAGTGAG CCTTACAACT         3151
Gln Thr Val Met Ser
            595
```

```
GCCTGTTCGT CTGTATATAC TTATTCTATC TTCGATACCC AATTCCATTG GAATTTCTTC    3211

CAGGATACAT GTCCCTGATC AGTATACCAT TTCACGTCCA CATTCAATCT TCAGCAACAC    3271

GAATTTATCC AAACCAATCA CCACCCTAGA TCTACCACAA CACTACCTTT ATACATATCT    3331

ACTTGATACC CAATCCCATT CCAACCAGGC GCAAAAGGCG TGCCCAGTCC AAATCAAAAT    3391

CAGCCCCCCG AGCCCAACCC TCTCCACATA TCCATACCCT AATCAAAATC ACCTTAATCT    3451

AAACAAATCC ATCACGCCCA AGGACCCCAC AGACCTCCCC TTCCCAACCC ACCCAGTCCA    3511

CCTCCACAAA CCAAACCCCA AATCAGAACT GCCGTGCAAC TCTCCGTCTT AGAACTCGCC    3571

CTTCGGTCCC GTCCCGAACT TAGATGGGCT TCGGGACGGC TTGCTGTATG CACTATGCAT    3631

GTAGTACGGA GTACGCCGTA CACATGTAGT AGGGGATATA TGTATGTACT ATGTACGCAT    3691

GTTCGAGTAC GCAGTACGTA GTGTGGCATG CAGGTCAGCT AGCATTGGCA GTAGCATATA    3751

CGGCATAACC TACGCTATGC ATCTAATATT CTTCGGTATA TACCCATGG TACGGAATTA     3811

GATGCAATAC ATGTACATGT ACATGTGCAT ACCTAGGTAC AAAGTGAATC TCGTTATTGT    3871

ATGTCTAGTC GTGTATAAGT GTAGTCCCAT GTCATATATA CAAGCCCATA CCGCATCGGA    3931

GCAAACCAGC CCATTCAGAC ATCCCTGCTC GAAACCCAGT CTACGGATTG AGACCGGGCT    3991

GAGCTGGGGT TTGGGTGTTG CTGCATGCGT ACGCCTACAT ACGTAGGGAG ATATGTTGCA    4051

CAGGATGCAG GGAATGACAA ATTGACGAAT TGAGAAATAC GCGAGTGGTT AGATGTTAAT    4111

TCTCGTTCGG GATGTTTATG TTTACCTAGG TATACTGGCT GGGGGGTCGT CATACACGTG    4171

GGAATTTGTG GCAATCTGTC AGTGGCCAGG TCCTTGTTTG ATTTATATGT TTGGGATGGG    4231

GATGGTCAAT GGGTATTCCA AGGAGGATGT ATCATCTGCT TTACACCGTC CCTTGCCTGG    4291

GATTTGGATT GAATTCTTCT TTCCACGTCG ATGTAGATTC TTCCCCGGAG CTATTCGGGT    4351

ACAACCCTGG CTTCCATATA TCATGTGTCC ATACTAAGTA CAGACGCTTC GATTTCCGGT    4411

GCTGCGAGTA GATCGGGAAC TGATCTCGCA TGTCTGTACA CGAAGGGTTG TACAAGCACG    4471

CGGTCGTTCT GCGTAACCGG TTGTTTATGT TATTGGATTT GGTATTCGTC TAATATGGAT    4531

GATTTGGGAT AAGCTTCTAT CCTGGGAATG GGTGCTTGGT ATAGTTCAGC CTAGTACTTC    4591

GTCTTCTATG TGATATTTCC AAAATAGTAG TTTTCGGTAA GTATATCTCC TACCTTTGAC    4651

TTTGGTTTGT GGTTTACGTC TTACCTGGCG TTTAGAGGGA GGGATAGGTT TCTGTATCAC    4711

CGTCGTGTTT CAACGTGGAT CGGGGTCCTT TCCCTGATAT ATATCTTGGC TTATGTTTCG    4771

TGCGGTAGTG CGGGTTCGTA TAATGCATGT CTGGTATATC ATACGGCATT AGTGACTGGG    4831

ACGTTGAGGT CGAGCTTGGT TTGAGGTTAC ATATATTGAG CCAAAATGGT CGAAAATATA    4891

TATCAACATT GCCAAAACAG AACTTCATTC GTTGGATGCC ATGCCAAATT GCTAATAGGT    4951

CTTGATCTTA CTCTGACTCC TATCTCATCT CACCTTGGTT ATTCGTTACA CAGCATTAAC    5011

CCCAAGAACC AGGTATAGTC TGATCGTGGA TGTGGGCCAC GACAAAATAG AAGGTCTCGT    5071

GTTTAGGGCG ACGAATCTGG GACTGCATTC CAGACGGGCC TGCGGAGAAT TTGCAGCATT    5131

TTATATCTAC ATGGTTGTTC CCTGGTGTGT GTGGGTGTTT CATGATATAT CCTGGTCGAT    5191

TCTGACGTGC GTATGTATCG CTGGAAAGGC TCGTAGGGGC TGCGTCGAC             5240
```

(2) INFORMATION FOR SEQ ID NO: 3

(i) SEQUENCE CHARACTERISTICS:
        (A) LENGTH: 2994 base pairs
        (B) TYPE: nucleotides
        (C) STRANDEDNESS: double
        (D) TOPOLOGY: linear -continued (ii) MOLECULE TYPE: genomic DNA (iii) HYPOTHETICAL: NO (iv) ANTI-SENSE: NO (vi) ORIGINAL SOURCE:
    (A) ORGANISM: Penicillium chrysogenum (vii) IMMEDIATE SOURCE:
    (B) CLONE: plasmids pALP315 and pALP316

(ix) FEATURE:
    (A) NAME/KEY: coding sequence
    (B) LOCATION: join (494...500, 617...647, 846...901,
        1047...1077, 1181...1952, 2022...2249)

(ix) FEATURE:
    (A) NAME/KEY: intron
    (B) LOCATION: 501...616

(ix) FEATURE:
    (A) NAME/KEY: intron
    (B) LOCATION: 648...845

(ix) FEATURE:
    (A) NAME/KEY: intron
    (B) LOCATION: 902...1046

(ix) FEATURE:
    (A) NAME/KEY: intron
    (B) LOCATION: 1078...1180

(ix) FEATURE:
    (A) NAME/KEY: intron
    (B) LOCATION: 1953...20216
    (D) OTHER INFORMATION: act gene (xi) SEQUENCE DESCRIPTION: SEQ ID NO: 3

```
GAATTCAGCA GCCTACGGAG TCCATAAGAC ACCAAGACAC AGCCATTGTA TGGATTATAT     60

ATGCCATGTA TGCCTGACAA TGCTGTATAA GTACTGTAAT ACAAGGTAAA CCCCCAACCC    120

GGTCAAGGTA CGTGTTCCCG CCGTACCCAA AAGGGTCCCC AAGAATGTCC ACGCAATACT    180

TTTAGGTAGA CATTGAAGGA ATCCAAGTGA GAAATTCAAT GAACATGAAC AATAGTTCTG    240

CCTTATAATC TTTATAAGTA TAAAAATCAG AAAGAGAATT ATATACAAAA GGGTAGATCT    300

GGAGGGGGTT CAGAGTTAAG GCCTCAGGCA GGCGCACAAT CCCAGCCATC ACAAACCCCT    360

CTCCACTCTT CCCTCTCTCT CTCTTCCTTC TTCCTTTCTC CCCTAATCCC AACTATATCC    420

CCTCTAACCT CTTTCCATCT TTCTTTTCTT TTTTCCCCTC TTCTCCCCTA AGTCCCTTGT    480

TTAATCAGTC ACA ATG GAG G GTATGTTATT CCAGTTGTGG CCACATCAGC AGCTTCCC   538
            Met Glu
             1

CGGAAGCTCC CCCCCCTGTT GGCCACAGCT TCGATTCCAT ATTTGCGAAT GACAACTAAC    598

CCGTATATCT CATTATAG  AA GAA GTT GCT GCT CTC GTC ATC GAC AAT GG      647
                    Glu Glu Val Ala Ala Leu Val Ile Asp Asn Gly
                     5                          10

GTATGTGCTA TACTTTTCCC CGGAGCTTCT GGCTTGTGTT GGGGTCGCCA ACTCAGCCCC    707

GGTCGCAGTC GTTGCCACCC CTAATCCGCC CGCGACGGCA GATGGAATCC ATCCCAATGG    767

CTTTCCATCT CGCTCCACAA CTACCAGAGG GTGATCCAAA GACTACAAGA ACTATGGATAC   827

TGATTATTTG CGATATAG T TCG GGT ATG TGT AAG GCC GGT TTC GCC GGT GAC    879
                      Ser Gly Met Cys Lys Ala Gly Phe Ala Gly Asp
                          15                      20

GAC GCA CCA CGA GCT GTT TTC C GTAAGTCCA ACCCCACAGA ATATGACACC        930
Asp Ala Pro Arg Ala Val Phe
25                  30
```

-continued

```
CCTCCTGTGC GAAGGCCGCC ATCCCACCAA CCCTTGCGTC GGATGGCTTC CCCTCTTTTG      990

CTTGGCTAGG AGGAACCTGG AACCTAGGAA ATCAAATAAC TGACAAAATT CAACAG         1046

CT TCC ATT GTC GGT CGT CCC CGC CAC CAT GG  GTAAATGATC CCCCCTTTTT     1097
   Pro Ser Ile Val Gly Arg Pro Arg His His Gly
                   35                  40

TTTCCGGCTC GTTTCGGCTG TATACGCTAT ACGCAGCCAA TTTGATCCCT AATGAACCAA    1157

AAAGAATACT AACATGGGCG CAG T ATT ATG ATT GGT ATG GGT CAG AAG GAC      1208
                          Ile Met Ile Gly Met Gly Gln Lys Asp
                                  45                  50

TCG TAC GTT GGT GAT GAG GCA CAG TCG AAG CGT GGT ATC CTC ACG CTC      1256
Ser Tyr Val Gly Asp Glu Ala Gln Ser Lys Arg Gly Ile Leu Thr Leu
            55                  60                  65

CGT TAC CCT ATT GAG CAC GGT GTT GTC ACC AAC TGG GAC GAC ATG GAG      1304
Arg Tyr Pro Ile Glu His Gly Val Val Thr Asn Trp Asp Asp Met Glu
        70                  75                  80

AAG ATC TGG CAC CAC ACC TTC TAC AAC GAG CTC CGT GTT GCC CCC GAA      1352
Lys Ile Trp His His Thr Phe Tyr Asn Glu Leu Arg Val Ala Pro Glu
        85                  90                  95

GAG CAC CCC ATT CTC TTG ACC GAA GCT CCC ATC AAC CCC AAG TTC AAC      1400
Glu His Pro Ile Leu Leu Thr Glu Ala Pro Ile Asn Pro Lys Phe Asn
100                 105                 110                 115

CGT GAG AAG ATG ACC CAG ATC GTG TTC GAG ACC TTC AAC GCC CCC GCC      1448
Arg Glu Lys Met Thr Gln Ile Val Phe Glu Thr Phe Asn Ala Pro Ala
                120                 125                 130

TTC TAC GTC TCC ATC CAG GCC GTT CTG TCC CTG TAC GCC TCC GGT CGT      1496
Phe Tyr Val Ser Ile Gln Ala Val Leu Ser Leu Tyr Ala Ser Gly Arg
            135                 140                 145

ACC ACT GGT ATC GTT CTC GAC TCC GGT GAC GGT GTC ACC CAC GTC GTC      1544
Thr Thr Gly Ile Val Leu Asp Ser Gly Asp Gly Val Thr His Val Val
            150                 155                 160

CCC ATC TAC GAG GGT TTC TCT CTG CCC CAC GCT ATC TCG CGT GTC GAC      1592
Pro Ile Tyr Glu Gly Phe Ser Leu Pro His Ala Ile Ser Arg Val Asp
165                 170                 175

ATG GCT GGC CGT GAT CTG ACC GAC TAC CTG ATG AAG ATC CTC GCT GAG      1640
Met Ala Gly Arg Asp Leu Thr Asp Tyr Leu Met Lys Ile Leu Ala Glu
180                 185                 190                 195

CGT GGT TAC ACT TTC TCC ACC ACC GCC GAG CGT GAA ATC GTC CGT GAC      1688
Arg Gly Tyr Thr Phe Ser Thr Thr Ala Glu Arg Glu Ile Val Arg Asp
                200                 205                 210

ATC AAG GAG AAG CTT TGC TAC GTC GCC CTC GAC TTC GAG CAG GAG ATC      1736
Ile Lys Glu Lys Leu Cys Tyr Val Ala Leu Asp Phe Glu Gln Glu Ile
            215                 220                 225

CAG ACC GCT TCC CAG AGC TCC AGC CTC GAG AAG TCC TAC GAG CTT CCC      1784
Gln Thr Ala Ser Gln Ser Ser Ser Leu Glu Lys Ser Tyr Glu Leu Pro
            230                 235                 240

GAT GGA CAG GTC ATC ACT ATT GGC AAC GAG CGC TTC CGT GCT CCT GAG      1832
Asp Gly Gln Val Ile Thr Ile Gly Asn Glu Arg Phe Arg Ala Pro Glu
245                 250                 255

GCT CTG TTC CAG CCT AAC GTT CTT GGC CTC GAG TCT GGC GGT ATC CAC      1880
Ala Leu Phe Gln Pro Asn Val Leu Gly Leu Glu Ser Gly Gly Ile His
260                 265                 270                 275

GTC ACC ACC TTC AAC TCC ATC ATG AAG TGT GAT GTT GAT GTC CGT AAG      1928
Val Thr Thr Phe Asn Ser Ile Met Lys Cys Asp Val Asp Val Arg Lys
                280                 285                 290

GAT CTC TAC GGA AAC ATT GTC ATG GTAAGAAAAA AGCCTCCAGA GCTGATGTTG     1982
Asp Leu Tyr Gly Asn Ile Val Met
                295
```

-continued

```
CGCAAAGATC CCCACTAACA TACAACTCCT TTTTTTTAG TCT GGT GGT ACC ACC        2036
                                            Ser Gly Gly Thr Thr
                                                        300

ATG TAC CCC GGT ATC TCC GAC CGT ATG CAG AAG GAG ATC ACT GCT CTT       2084
Met Tyr Pro Gly Ile Ser Asp Arg Met Gln Lys Glu Ile Thr Ala Leu
305                 310                 315                 320

GCT CCT TCT TCC ATG AAG GTC AAG ATC ATC GCT CCC CCC GAG CGC AAG       2132
Ala Pro Ser Ser Met Lys Val Lys Ile Ile Ala Pro Pro Glu Arg Lys
                325                 330                 335

TAC TCC GTC TGG ATC GGT GGA TCC ATT CTG GCC TCC CTG TCG ACC TTC       2180
Tyr Ser Val Trp Ile Gly Gly Ser Ile Leu Ala Ser Leu Ser Thr Phe
            340                 345                 350

CAG CAG ATG TGG ATC TCC AAG CAG GAG TAC GAC GAG AGC GGT CCT TCC       2228
Gln Gln Met Trp Ile Ser Lys Gln Glu Tyr Asp Glu Ser Gly Pro Ser
        355                 360                 365

ATC GTT CAC CGC AAG TGC TTC TAAGCTTCTT GCAGCACTTT ACTACTCGTA          2279
Ile Val His Arg Lys Cys Phe
    370             375

TTCGCTCGTA CTTTCCTGGT GTATCAAAAA GCAGGATGGA GGCACTGGTG GATTGCAAGC     2339

GTTGTTGGAC TCGCATTATC AAGCGGATAG CCTGAAAATG GAATCTCGAT TTTAGTGGAA     2399

TAGAGTCGGT CGTTTTCTTT TTGTTACTCT TTACCTTACT CTTTACTCGA TCTCTATCCA     2459

TCCATTTCTG CTTTGAACCA TTTCACCTTT ACTCCATCTT TTTCCCTTTC CTCATTCGAA     2519

TCCGCTGTCC CGTCCACCTC TCTGATTGTT TTGCCTGGAC GGGTCTCTGG CGATGCGGCA     2579

TCAACAGTGT ACCTGTAGGG CAAGGATGTA TATGGAGTTG GTTGGCTATA GGGATTAGGT     2639

TGCGTTGTCC TTTTCGACGT CTTCTACGTC TTTGTTCTAG CCCCTTGCGT TGTCTTCAAC     2699

TAAACTGCCC TTGTCCGTAG CTTTTAACGT GACTTTGACT TCAAATATTC CACTGGTTCC     2759

TTGTATTCTG CTAGAAACGC TGGTTCAACG CTTGTTGAAT GTCTTCTATG TCCAACATCT     2819

ACAAGACGTA TCCGAGAAGA CAACAAAAAG GCTCTGAGGA AAGTCTACTA AAACTTGGC     2879

CAGGCCGGAT TAGGCCTTTG TCATGGTTAT TGTACTGTCA TTCGATCAGT CCATATTGAT     2939

ATTCTGGGAA TATGTAGGCT GACGAGATAA ATGGCACGCA TTGGGTGTGT ATCTT          2994
```

(2) INFORMATION FOR SEQ ID NO: 4

(i) SEQUENCE CHARACTERISTICS:
        (A) LENGTH: 3240 base pairs
        (B) TYPE: nucleotides
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Penicillum chrysogenum (vii) IMMEDIATE SOURCE:
        (B) CLONE: <Unknown>

(ix) FEATURE:
        (A) NAME/KEY: intron
        (B) LOCATION: 794...920

(ix) FEATURE:
        (A) NAME/KEY: intron
        (B) LOCATION: 952...1123

(ix) FEATURE:
        (A) NAME/KEY: intron (B) LOCATION: 1180...1289

(ix) FEATURE:
                    (A) NAME/KEY: intron
                    (B) LOCATION: 1321...1410

(ix) FEATURE:
                    (A) NAME/KEY: intron
                    (B) LOCATION: 2183...2249
                    (D) OTHER INFORMATION: act gene (xi) SEQUENCE DESCRIPTION: SEQ ID NO: 4

```
GCCAGGCTGG CACCGGCCTG CCTTGATGCG AGATGCCTAC TCGTACTATG CCTACAGGTA      60

TGGGCTTTCC GCGTGTCGTC AGCTTGCGAC CGCGCGGCTG CTGACGACCC AAGGCAAGCT     120

GGTAACATGG CGGCACGAAA TTTCTCTCTG CCTGCTCGTC CTCTTGGTGT GGAGGGGTAC     180

GAGTGCAGGT ATGATGGGAC GGCAGAGGAG TGACGGAGGC TGTGCGGTTG CACGAGTAC      240

TGTACGAGTA CTCGTACTGT AGGTGCAGCG ACTGTGGTGG TACTGCTAGG TGGAATTGGG     300

TCCAGCAGGC ATGCAGCTCC CAGCCACCGT CGTTAACCAA TCAGTTAAAG CAGCAACGCA     360

ACCCGCCCCC GTTTTTCTGC AGAAATTTG GCGGTGTCG TGCCCCAGT CGCTGTTGCC       420

CGCCCTTGTC TGGTCGCCTA CAGGCTGCAC ACAGGTAAC AACAGCCCGC CCCAGGTCCT     480

TGTAGGTGCC CAGTGAGTGC CCGGTGCCCA CAAGTTTCTC GTGGCATCCA CTGGCGGACT    540

TGGAAGCCCA TCAGTGATGC TTCCCTCCTT TCCCCCTCCA CATCTCACTC AGCTCACGCA    600

AGCCAACCCT CTCTCCCCCC GTCTCCATTC CATCTTCTTC TCTCCACGAC CCTTAAGAGT    660

CCCTCCTGCT CACGTCGACC ATCCTTCGCT CCCAGCCCCA CGACATCTGC ATCGTCTGGG    720

CTTCTTGACA CTCTGTCATT TCTTCCTTAT AAAACCTCTT TACCGCTCTT CCCGTAATCC    780

GACGCC ATG GAG G GTACGTGTCG CCGCAACGCA CTCCCGCTTC CCCTACTACC CCTA     837
       Met Glu
         1

TCGCGC ATCCACACGG CGCCGCGATG CCTAGCCATC GCGAGGGTGC ATCGCAACGA CTT     896

GGCTAAC TGTTCTTCGC TTCACAG AG GAG GTC GCC GCC CTC GTT ATC GAC          946
                             Glu Glu Val Ala Ala Leu Val Ile Asp
                                    5                  10

AAT GG GTAAGCTCGC CCGCTGTCTC ACCGACATCC ATCGTCCCCC TGGCCTCTGT         1001
Asn Gly

CGAGATGGGA GCCTCCAGGG GTCCCTTCGA CGAGCGCGTC GATTGCCAAA ATCCAACGAG    1061

ATCGGGCCAT ACTGAGCCGA CACTCGTGTG TTTTCTGGAC ATTAGGACTG ACTTGATTCT    1121

AG T TCG GGT ATG TGC AAG GCC GGT TTC GCC GGT GAT GAT GCT CCC CGA     1169
    Ser Gly Met Cys Lys Ala Gly Phe Ala Gly Asp Asp Ala Pro Arg
     15                  20                  25

GCT GTT TTC C GTAAGTACCC CACTTCCACC CGTCGAGCTC CCCAATTGTC CACCGCCAGG 1229
Ala Val Phe
       30

GCGAGAAGGG GGCAGAACGG GGCAAACTGC ATCGCAAACA TGGCTAATTC GATGCGACAG    1289

CG TCC ATT GTC GGT CGT CCC CGC CAC CAT GG GTAAGTTTCC GGCCGCAGCC      1340
   Pro Ser Ile Val Gly Arg Pro Arg His His Gly
              35                  40

GACACCTCTC ACCCCCCCCC GGGGGGCTCC TAAGCGAGTC AGCGCTGGTT CTGACCGCTG    1400

GATACTATAG C ATC ATG ATC GGC ATG GGC CAG AAG GAC TCG TAC GTC GGT     1450
             Ile Met Ile Gly Met Gly Gln Lys Asp Ser Tyr Val Gly
                    45                  50                  55

GAC GAG GCT CAG TCC AAG CGT GGT ATC CTC ACC CTG CGC TAC CCC ATT      1498
Asp Glu Ala Gln Ser Lys Arg Gly Ile Leu Thr Leu Arg Tyr Pro Ile
         60                  65                  70
```

```
GAG CAC GGT GTT GTC ACC AAC TGG GAC GAC ATG GAG AAG ATC TGG CAC     1546
Glu His Gly Val Val Thr Asn Trp Asp Asp Met Glu Lys Ile Trp His
        75                  80                  85

CAC ACC TTC TAC AAC GAG CTG CGT GTT GCC CCC GAG GAG CAC CCG GTC     1594
His Thr Phe Tyr Asn Glu Leu Arg Val Ala Pro Glu Glu His Pro Val
        90                  95                  100

CTG CTC ACC GAG GCG CCC ATC AAC CCC AAG TCC AAC CGT GAG AAG ATG     1642
Leu Leu Thr Glu Ala Pro Ile Asn Pro Lys Ser Asn Arg Glu Lys Met
        105                 110                 115

ACC CAG ATC GTC TTC GAG ACC TTC AAC GCC CCT GCC TTC TAC GTC TCC     1690
Thr Gln Ile Val Phe Glu Thr Phe Asn Ala Pro Ala Phe Tyr Val Ser
120                 125                 130                 135

ATC CAG GCC GTC CTG TCA CTG TAC GCC TCC GGC CGT ACG ACC GGT ATC     1738
Ile Gln Ala Val Leu Ser Leu Tyr Ala Ser Gly Arg Thr Thr Gly Ile
                140                 145                 150

GTC CTG GAC TCT GGT GAT GGT GTC ACC CAC GTT GTC CCC ATC TAC GAG     1786
Val Leu Asp Ser Gly Asp Gly Val Thr His Val Val Pro Ile Tyr Glu
                155                 160                 165

GGT TTC GCC CTG CCC CAC GCC ATT GCC CGT GTC GAC ATG GCT GGT CGT     1834
Gly Phe Ala Leu Pro His Ala Ile Ala Arg Val Asp Met Ala Gly Arg
        170                 175                 180

GAT CTC ACC GAC TAC CTC ATG AAG ATC CTG GCC GAG CGC GGC TAC ACC     1882
Asp Leu Thr Asp Tyr Leu Met Lys Ile Leu Ala Glu Arg Gly Tyr Thr
        185                 190                 195

TTC TCC ACC ACG GCC GAG CGT GAG ATT GTC CGT GAC ATC AAG GAG AAG     1930
Phe Ser Thr Thr Ala Glu Arg Glu Ile Val Arg Asp Ile Lys Glu Lys
200                 205                 210                 215

CTC TGC TAC GTC GCC CTC GAC TTC GAG CAG GAG ATC CAG ACT GCC GCC     1978
Leu Cys Tyr Val Ala Leu Asp Phe Glu Gln Glu Ile Gln Thr Ala Ala
                220                 225                 230

CAG AGC TCC AGC CTG GAG AAG TCC TAC GAG CTT CCC GAC GGC CAG GTC     2026
Gln Ser Ser Ser Leu Glu Lys Ser Tyr Glu Leu Pro Asp Gly Gln Val
                235                 240                 245

ATC ACC ATT GGC AAT GAG CGC TTC CGT GCT CCC GAG GCT CTC TTC CAG     2074
Ile Thr Ile Gly Asn Glu Arg Phe Arg Ala Pro Glu Ala Leu Phe Gln
        250                 255                 260

CCC TCC GTC CTG GGT CTC GAG AGC GGC GGC ATC CAC GTC ACC ACC TTC     2122
Pro Ser Val Leu Gly Leu Glu Ser Gly Gly Ile His Val Thr Thr Phe
        265                 270                 275

AAC TCC ATC ATG AAG TGC GAC GTC GAT GTC CGT AAG GAT CTG TAC GGC     2170
Asn Ser Ile Met Lys Cys Asp Val Asp Val Arg Lys Asp Leu Tyr Gly
280                 285                 290                 295

AAC ATT GTC ATG GTAAGTCAGA TGCCGGGCCT GGAAGACACC TCATTTAGGA TCT     2225
Asn Ile Val Met

TGCTAAC ACCAATTTTT TTTTTAG TCT GGT GGT ACC ACC ATG TAC CCT GGC     2276
                        Ser Gly Gly Thr Thr Met Tyr Pro Gly
                                300                 305

CTC TCT GAC CGT ATG CAG AAG GAG ATC ACT GCT CTT GCT CCT TCT TCC     2324
Leu Ser Asp Arg Met Gln Lys Glu Ile Thr Ala Leu Ala Pro Ser Ser
        310                 315                 320

ATG AAG GTC AAG ATC ATT GCT CCC CCG GAG CGC AAG TAC TCC GTC TGG     2372
Met Lys Val Lys Ile Ile Ala Pro Pro Glu Arg Lys Tyr Ser Val Trp
325                 330                 335                 340

ATC GGT GGT TCC ATT CTG GCG TCT CTG TCC ACC TTC CAG CAG ATG TGG     2420
Ile Gly Gly Ser Ile Leu Ala Ser Leu Ser Thr Phe Gln Gln Met Trp
                345                 350                 355

ATC TCG AAG CAG GAG TAC GAC GAG AGC GGC CCC TCC ATC GTC CAC CGC     2468
Ile Ser Lys Gln Glu Tyr Asp Glu Ser Gly Pro Ser Ile Val His Arg
        360                 365                 370
```

-continued

```
AAG TGC TTC TAAGGTATGT TGTCGTCGGG AAGCCGGATA CCCGAATGTA AGGTTGACAG  2527
Lys Cys Phe
        375

GTTCGAAAAG ACAAGGCAAC CGGCCAGAAC CAAATCCTTC CACCCTCCGC AAAAGAACGC  2587

CAAGATGTCG GAGTCGGTGG CGACCGATGC AACGTCTACT CACGTGCGCG CGTATCCCAC  2647

TCAAGTCTCA TATTTACGAA AAGTTATTTC ACATGGTCAG GCGGTGGTGG GCGTTGCCTT  2707

TTCTCGGAAC AGACATGACG GCGGCCACTT TTGTAGTCGG ATGCGTTTAG GGATGCGAGC  2767

CTAGGGGTGT AGGAAGCTGA GGTTGATATA CAATAACTTT TTTTGCTTTC CGTTCTAGAC  2827

TCGTTCAATG GGAAGACGTG ACGGAATCGC TTGGCTGTCT AATAGCCAGC TTGATCAGGC  2887

GAGTCGGGTT GTTGTGTTTC GATGTTGAGA GGTGCACCAG CGTATTTGTA TGGCCGAGGT  2947

AGGTATTATG GTCTCGTATT TGCAACACTA GAGCTCGCTT GCTCGTTTTT ACCAGCAGTG  3007

TCCTCTGCCA TGCCGCGGCT CCGACTCTCG TCTGGCTTCT CAGACCGTGC CTCGTCAATA  3067

GTATTATCCC CCGTAGTAAC CTCCGCACTA GCCGGTTCTT TGTCGTCTTC CTGCTCGCCG  3127

ATGAGCTTCC TGTACTTGCG CCTCTTCTTC TTGTCGGCGC TGGCAGCCCT CTTCTGCTTG  3187

ATGCGCCCGA CCATGGCGGA CCGGCTCTGC TCCCCGTTGA GCAGCTCGTC GAC         3240
```

(2) INFORMATION FOR SEQ ID NO: 5

(i) SEQUENCE CHARACTERISTICS:
        (A) LENGTH: 461 amino acids
        (B) TYPE: amino acids
        (C) STRANDEDNESS: single
        (D) TOPOLOGY: linear (ii) MOLECULE TYPE: peptide (vi) ORIGINAL SOURCE:
        (A) ORGANISM: Penicillum chrysogenum (ix) FEATURE:
        (D) OTHER INFORMATION: amino acid sequence of the
            glutamate dehydrogenase enzyme
        (EC.1.4.1.4) with a molecular weight
            of 49837 Da.

(xi) SEQUENCE DESCRIPTION: SEQ ID NO: 5

```
Met Met Gln Asn Leu Pro Phe Glu Pro Glu Phe Glu Gln Ala Tyr
1               5                   10                  15

Lys Glu Leu Ala Ser Thr Leu Glu Asn Ser Thr Leu Phe Gln Lys
                20                  25                  30

Lys Pro Glu Tyr Arg Lys Ala Leu Gln Val Val Ser Val Pro Glu
                35                  40                  45

Arg Val Ile Gln Phe Arg Val Val Trp Glu Asp Asp Lys Gly Gln
                50                  55                  60

Val Gln Ile Asn Arg Gly Tyr Arg Val Gln Phe Asn Ser Ala Leu
                65                  70                  75

Gly Pro Tyr Lys Gly Gly Leu Arg Phe His Pro Thr Val Asn Leu
                80                  85                  90

Ser Ile Leu Lys Phe Leu Gly Phe Glu Gln Ile Phe Lys Asn Ala
                95                  100                 105

Leu Thr Gly Leu Asn Met Gly Gly Gly Lys Gly Ser Asp Phe
                110                 115                 120

Asp Pro Lys Gly Lys Thr Asp Asn Glu Ile Arg Arg Phe Cys Val
                125                 130                 135

Ser Phe Met Thr Glu Leu Cys Lys His Ile Gly Ala Asp Thr Asp
```

```
                140                 145                 150
Val Pro Ala Gly Asp Ile Gly Val Thr Gly Arg Glu Val Gly Phe
            155                 160                 165
Met Phe Gly Gln Tyr Lys Lys Ile Arg Asn Gln Trp Glu Gly Val
            170                 175                 180
Leu Thr Gly Lys Gly Gly Ser Trp Gly Gly Ser Leu Ile Arg Pro
            185                 190                 195
Glu Ala Thr Gly Tyr Gly Val Val Tyr Val Glu His Met Ile
            200                 205                 210
Gln His Ala Ser Gly Gly Lys Glu Ser Phe Ala Gly Lys Arg Val
            215                 220                 225
Ala Ile Ser Gly Ser Gly Asn Val Ala Gln Tyr Ala Ala Leu Lys
            230                 235                 240
Val Ile Glu Leu Gly Gly Ser Val Ile Ser Leu Ser Asp Ser Gln
            245                 250                 255
Gly Ala Leu Val Leu Asn Gly Glu Glu Gly Ser Phe Thr Ala Glu
            260                 265                 270
Glu Ile Asn Thr Ile Ala Glu Ile Lys Val Gln Arg Lys Gln Ile
            275                 280                 285
Ala Glu Leu Ala Thr Gln Asp Ala Phe Ser Ser Lys Phe Lys Tyr
            290                 295                 300
Ile Pro Gly Ala Arg Pro Trp Thr Asn Ile Ala Gly Arg Ile Asp
            305                 310                 315
Val Ala Leu Pro Ser Ala Thr Gln Asn Glu Val Ser Gly Asp Glu
            320                 325                 330
Ala Lys Ala Leu Ile Ala Ala Gly Cys Lys Phe Ile Ala Glu Gly
            335                 340                 345
Ser Asn Met Gly Ser Thr Gln Glu Ala Ile Asp Val Phe Glu Ala
            350                 355                 360
His Arg Asp Ala Asn Pro Gly Ala Ala Ala Ile Trp Tyr Ala Pro
            365                 370                 375
Gly Lys Ala Ala Asn Ala Gly Gly Val Ala Val Ser Gly Leu Glu
            380                 385                 390
Met Ala Gln Asn Ser Ala Arg Val Asn Trp Ser Arg Glu Glu Val
            395                 400                 405
Asp Ser Arg Leu Lys Lys Ile Met Glu Asp Cys Phe Asn Asn Gly
            410                 415                 420
Leu Ser Thr Ala Lys Glu Tyr Val Thr Pro Ala Glu Gly Val Leu
            425                 430                 435
Pro Ser Leu Val Ala Gly Ser Asn Ile Ala Gly Phe Thr Lys Val
            440                 445                 450
Ala Glu Ala Met Lys Glu His Gly Asp Trp Trp
            455                 460

(2) INFORMATION FOR SEQ ID NO: 6

(i) SEQUENCE CHARACTERISTICS:
        (A) LENGTH: 596 amino acids
        (B) TYPE: amino acids
        (C) STRANDEDNESS: single
        (D) TOPOLOGY: linear (ii) MOLECULE TYPE: peptide (vi) ORIGINAL SOURCE:
        (A) ORGANISM: Penicillum chrysogenum
```

(ix) FEATURE:
    (D) OTHER INFORMATION: amino acid sequence of the -N-acetylhexosaminidase enzyme
        (EC.3.2.1.52) with a
        molecular weight of 66545 Da.

(xi) SEQUENCE DESCRIPTION: SEQ ID NO: 6

```
Met Lys Phe Ala Ser Val Leu Asn Val Leu Gly Ala Leu Thr Ala
1               5                   10                  15

Ala Ser Ala Val Gln Val Asn Pro Leu Pro Ala Pro Arg Asn Ile
                20                  25                  30

Thr Trp Gly Ser Ser Gly Pro Ile Gln Val Asn Asn Leu Asn Leu
                35                  40                  45

Asn Gly Pro His Ser Pro Leu Leu Thr Gln Ala Trp Glu Arg Ala
                50                  55                  60

Trp Glu Thr Ile Thr Thr Leu Gln Trp Val Pro Ala Ala Val Glu
                65                  70                  75

Ser Pro Ile Ala Ser Tyr Pro Ala Phe Pro Thr Ser Thr Pro Val
                80                  85                  90

Ser Ser Ala Pro Lys Ala Lys Arg Ala Pro Ser Gly Ile His Asn
                95                  100                 105

Val Asp Val His Val Asp Asn Asp Ala Asp Leu Gln Tyr Gly
                110                 115                 120

Val Asp Glu Ser Tyr Thr Leu Val Val Ser Asp Gly Gly Ile Arg
                125                 130                 135

Ile Asn Ser Gln Thr Val Trp Gly Val Leu Gln Ala Phe Thr Thr
                140                 145                 150

Leu Gln Gln Ile Ile Ile Ser Asp Gly Lys Gly Gly Leu Ile Ile
                155                 160                 165

Glu Gln Pro Val Lys Ile Lys Asp Ala Pro Leu Tyr Pro His Arg
                170                 175                 180

Gly Ile Met Ile Asp Thr Gly Arg Asn Phe Ile Thr Val Arg Lys
                185                 190                 195

Leu Leu Glu Gln Ile Asp Gly Met Ala Leu Ser Lys Leu Asn Val
                200                 205                 210

Leu His Trp His Leu Asp Asp Ser Gln Ser Trp Pro Met Gln Met
                215                 220                 225

Ser Ser Tyr Pro Glu Met Thr Lys Asp Ala Tyr Ser Pro Arg Glu
                230                 235                 240

Ile Tyr Thr Glu His Asp Met Arg Arg Val Ile Ala Tyr Ala Arg
                245                 250                 255

Ala Arg Gly Val Arg Val Ile Pro Glu Val Asp Met Pro Ala His
                260                 265                 270

Ser Ala Ser Gly Trp Gln Gln Val Asp Pro Glu Ile Val Ala Cys
                275                 280                 285

Ala Glu Ser Trp Trp Ser Asn Asp Val Trp Ala Glu His Thr Ala
                290                 295                 300

Val Gln Pro Asn Pro Gly Gln Leu Asp Ile Ile Tyr Pro Lys Thr
                305                 310                 315

Tyr Glu Val Val Asn Asn Val Tyr Gln Glu Leu Ser Arg Ile Phe
                320                 325                 330

Ser Asp Asn Leu Phe His Val Gly Ala Asp Glu Ile Gln Pro Asn
                335                 340                 345

Cys Tyr Asn Tyr Ser Thr His Ile Thr Lys Trp Phe Ala Glu Asp
                350                 355                 360
```

-continued

```
Pro Ser Arg Thr Tyr Asn Asp Leu Ala Gln Tyr Trp Val Asp His
            365                 370                 375
Ser Met Pro Ile Phe Arg Ser Val Gly Asp His Arg Arg Leu Met
            380                 385                 390
Met Trp Glu Asp Ile Ala Ile Ala Thr Glu Ser Ala His Asp Val
            395                 400                 405
Pro Lys Asp Val Ile Met Gln Thr Trp Asn Ser Gly Glu Gly Glu
            410                 415                 420
Gly Asn Ile Lys Lys Leu Thr Ser Ala Gly Tyr Asp Val Val Val
            425                 430                 435
Ser Thr Ser Asp Phe Leu Tyr Leu Asp Cys Gly Arg Gly Gly Tyr
            440                 445                 450
Val Thr Asn Asp Ala Arg Tyr Asn Val Gln Ser Asn Thr Asp Gly
            455                 460                 465
Gly Val Asn Phe Asn Tyr Gly Gly Asp Gly Gly Ser Trp Cys Ala
            470                 475                 480
Pro Tyr Lys Thr Trp Gln Arg Ile Tyr Asp Tyr Asp Phe Leu Thr
            485                 490                 495
Asn Leu Thr Ser Ser Glu Ala Lys His Ile Ile Gly Ala Glu Ala
            500                 505                 510
Pro Leu Trp Ser Glu Gln Val Asp Asp Val Thr Val Ser Ser Val
            515                 520                 525
Phe Trp Pro Arg Ala Ala Ala Leu Gly Glu Leu Val Trp Ser Gly
            530                 535                 540
Asn Arg Asp Ala Ala Gly Arg Lys Arg Thr Thr Ser Phe Thr Gln
            545                 550                 555
Arg Ile Leu Asn Phe Arg Glu Tyr Leu Val Ala Asn Gly Val Met
            560                 565                 570
Ala Thr Ala Leu Val Pro Lys Tyr Cys Leu Gln His Pro His Ala
            575                 580                 585
Cys Asp Leu Tyr Lys Asn Gln Thr Val Met Ser
            590                 595
```

(2) INFORMATION FOR SEQ ID NO: 7

(i) SEQUENCE CHARACTERISTICS:
        (A) LENGTH: 375 amino acids
        (B) TYPE: amino acids
        (C) STRANDEDNESS: single
        (D) TOPOLOGY: linear (ii) MOLECULE TYPE: peptide (vi) ORIGINAL SOURCE:
        (A) ORGANISM: Penicillium chrysogenum (ix) FEATURE:
        (D) OTHER INFORMATION: amino acid sequence of the -actin protein with a molecular weight of 41760 Da.

(xi) SEQUENCE DESCRIPTION: SEQ ID NO: 7

```
Met Glu Glu Glu Val Ala Ala Leu Val Ile Asp Asn Gly Ser Gly
1               5                   10                  15
Met Cys Lys Ala Gly Phe Ala Gly Asp Asp Ala Pro Arg Ala Val
                20                  25                  30
Phe Pro Ser Ile Val Gly Arg Pro Arg His His Gly Ile Met Ile
                35                  40                  45
```

```
Gly Met Gly Gln Lys Asp Ser Tyr Val Gly Asp Glu Ala Gln Ser
                50                  55                  60

Lys Arg Gly Ile Leu Thr Leu Arg Tyr Pro Ile Glu His Gly Val
                65                  70                  75

Val Thr Asn Trp Asp Asp Met Glu Lys Ile Trp His Thr Phe
                80                  85                  90

Tyr Asn Glu Leu Arg Val Ala Pro Glu His Pro Ile Leu Leu
                95                 100                 105

Thr Glu Ala Pro Ile Asn Pro Lys Phe Asn Arg Glu Lys Met Thr
               110                 115                 120

Gln Ile Val Phe Glu Thr Phe Asn Ala Pro Ala Phe Tyr Val Ser
               125                 130                 135

Ile Gln Ala Val Leu Ser Leu Tyr Ala Ser Gly Arg Thr Thr Gly
               140                 145                 150

Ile Val Leu Asp Ser Gly Asp Gly Val Thr His Val Val Pro Ile
               155                 160                 165

Tyr Glu Gly Phe Ser Leu Pro His Ala Ile Ser Arg Val Asp Met
               170                 175                 180

Ala Gly Arg Asp Leu Thr Asp Tyr Leu Met Lys Ile Leu Ala Glu
               185                 190                 195

Arg Gly Tyr Thr Phe Ser Thr Thr Ala Glu Arg Glu Ile Val Arg
               200                 205                 210

Asp Ile Lys Glu Lys Leu Cys Tyr Val Ala Leu Asp Phe Glu Gln
               215                 220                 225

Glu Ile Gln Thr Ala Ser Gln Ser Ser Leu Glu Lys Ser Tyr
               230                 235                 240

Glu Leu Pro Asp Gly Gln Val Ile Thr Ile Gly Asn Glu Arg Phe
               245                 250                 255

Arg Ala Pro Glu Ala Leu Phe Gln Pro Asn Val Leu Gly Leu Glu
               260                 265                 270

Ser Gly Gly Ile His Val Thr Thr Phe Asn Ser Ile Met Lys Cys
               275                 280                 285

Asp Val Asp Val Arg Lys Asp Leu Tyr Gly Asn Ile Val Met Ser
               290                 295                 300

Gly Gly Thr Thr Met Tyr Pro Gly Ile Ser Asp Arg Met Gln Lys
               305                 310                 315

Glu Ile Thr Ala Leu Ala Pro Ser Ser Met Lys Val Lys Ile Ile
               320                 325                 330

Ala Pro Pro Glu Arg Lys Tyr Ser Val Trp Ile Gly Gly Ser Ile
               335                 340                 345

Leu Ala Ser Leu Ser Thr Phe Gln Gln Met Trp Ile Ser Lys Gln
               350                 355                 360

Glu Tyr Asp Glu Ser Gly Pro Ser Ile Val His Arg Lys Cys Phe
               365                 370                 375

(2) INFORMATION FOR SEQ ID NO: 8

(i) SEQUENCE CHARACTERISTICS:
        (A) LENGTH: 375 amino acids
        (B) TYPE: amino acids
        (C) STRANDEDNESS: single
        (D) TOPOLOGY: linear (ii) MOLECULE TYPE: Peptide (vi) ORIGINAL SOURCE:
        (A) ORGANISM: Acremonium chrysogenum
```

(ix) FEATURE:
    (D) OTHER INFORMATION:  amino acid sequence of the -actin
        protein with a molecular weight of
        41612 Da.

(xi) SEQUENCE DESCRIPTION: SEQ ID NO: 8

```
Met Glu Glu Val Ala Ala Leu Val Ile Asp Asn Gly Ser Gly
1               5                  10                  15

Met Cys Lys Ala Gly Phe Ala Gly Asp Asp Ala Pro Arg Ala Val
            20                  25                  30

Phe Pro Ser Ile Val Gly Arg Pro Arg His Gly Ile Met Ile
            35                  40                  45

Gly Met Gly Gln Lys Asp Ser Tyr Val Gly Asp Glu Ala Gln Ser
            50                  55                  60

Lys Arg Gly Ile Leu Thr Leu Arg Tyr Pro Ile Glu His Gly Val
            65                  70                  75

Val Thr Asn Trp Asp Asp Met Glu Lys Ile Trp His His Thr Phe
            80                  85                  90

Tyr Asn Glu Leu Arg Val Ala Pro Glu Glu His Pro Val Leu Leu
            95                  100                 105

Thr Glu Ala Pro Ile Asn Pro Lys Ser Asn Arg Glu Lys Met Thr
            110                 115                 120

Gln Ile Val Phe Glu Thr Phe Asn Ala Pro Ala Phe Tyr Val Ser
            125                 130                 135

Ile Gln Ala Val Leu Ser Leu Tyr Ala Ser Gly Arg Thr Thr Gly
            140                 145                 150

Ile Val Leu Asp Ser Gly Asp Gly Val Thr His Val Val Pro Ile
            155                 160                 165

Tyr Glu Gly Phe Ala Leu Pro His Ala Ile Ala Arg Val Asp Met
            170                 175                 180

Ala Gly Arg Asp Leu Thr Asp Tyr Leu Met Lys Ile Leu Ala Glu
            185                 190                 195

Arg Gly Tyr Thr Phe Ser Thr Thr Ala Glu Arg Glu Ile Val Arg
            200                 205                 210

Asp Ile Lys Glu Lys Leu Cys Tyr Val Ala Leu Asp Phe Glu Gln
            215                 220                 225

Glu Ile Gln Thr Ala Ala Gln Ser Ser Ser Leu Glu Lys Ser Tyr
            230                 235                 240

Glu Leu Pro Asp Gly Gln Val Ile Thr Ile Gly Asn Glu Arg Phe
            245                 250                 255

Arg Ala Pro Glu Ala Leu Phe Gln Pro Ser Val Leu Gly Leu Glu
            260                 265                 270

Ser Gly Gly Ile His Val Thr Thr Phe Asn Ser Ile Met Lys Cys
            275                 280                 285

Asp Val Asp Val Arg Lys Asp Leu Tyr Gly Asn Ile Val Met Ser
            290                 295                 300

Gly Gly Thr Thr Met Tyr Pro Gly Leu Ser Asp Arg Met Gln Lys
            305                 310                 315

Glu Ile Thr Ala Leu Ala Pro Ser Ser Met Lys Val Lys Ile Ile
            320                 325                 330

Ala Pro Pro Asp Gly Lys Tyr Ser Val Trp Ile Gly Gly Ser Ile
            335                 340                 345

Leu Ala Ser Leu Ser Thr Phe Gln Gln Met Trp Ile Ser Lys Thr
            350                 355                 360
```

Glu Tyr Asp Glu Glu Arg Pro Ser Ile Val His Arg Lys Cys Phe
                365                 370                 375

(2) INFORMATION FOR SEQ ID NO: 9

(i) SEQUENCE CHARACTERISTICS:
        (A) LENGTH: 22 amino acids
        (B) TYPE: amino acids
        (C) STRANDEDNESS: single
        (D) TOPOLOGY: linear (ii) MOLECULE TYPE: Peptide (vi) ORIGINAL SOURCE:
        (A) ORGANISM: Penicillum chrysogenum (xi) SEQUENCE DESCRIPTION: SEQ ID NO: 9

Ala Pro Ser Gly Ile His Asn Val Asp Val His Val Val Asp Asn Asp Ala
                5                   10                  15
Gln Tyr Gly
20

(2) INFORMATION FOR SEQ ID NO: 10

(i) SEQUENCE CHARACTERISTICS:
        (A) LENGTH: 22 amino acids
        (B) TYPE: amino acids
        (C) STRANDEDNESS: single
        (D) TOPOLOGY: linear (ii) MOLECULE TYPE: Peptide (vi) ORIGINAL SOURCE:
        (A) ORGANISM: Penicillum chrysogenum (xi) SEQUENCE DESCRIPTION: SEQ ID NO: 10

Val Gln Val Asn Pro Leu Pro Ala Pro Arg Arg Ile Thr Xaa Gly
                5                   10                  15
Ser Ser Gly Pro Xaa Xaa Val
                20

(2) INFORMATION FOR SEQ ID NO: 11

(i) SEQUENCE CHARACTERISTICS:
        (A) LENGTH: 32 base pairs
        (B) TYPE: nucleotides
        (C) STRANDEDNESS: single
        (D) TOPOLOGY: linear (xi) SEQUENCE DESCRIPTION: SEQ ID NO: 11

TCGACGACGT GSACGTCSAC GTTGTGGATG CC                                    32

(2) INFORMATION FOR SEQ ID NO: 12

(i) SEQUENCE CHARACTERISTICS:
        (A) LENGTH: 32 base pairs
        (B) TYPE: nucleotides
        (C) STRANDEDNESS: single
        (D) TOPOLOGY: linear (xi) SEQUENCE DESCRIPTION: SEQ ID NO: 12

CCGTAYTGSA GGTCRGCGTC GTTGTCGACG AC                                    32

(2) INFORMATION FOR SEQ ID NO: 13

(i) SEQUENCE CHARACTERISTICS:
        (A) LENGTH: 23 base pairs (B) TYPE: nucleotides
        (C) STRANDEDNESS: single
        (D) TOPOLOGY: linear (xi) SEQUENCE DESCRIPTION: SEQ ID NO: 13

GGGGCVGGSA GVGGGTTGAC YTG                                              23

(2) INFORMATION FOR SEQ ID NO: 14

(i) SEQUENCE CHARACTERISTICS:
        (A) LENGTH: 28 base pairs
        (B) TYPE: nucleotides
        (C) STRANDEDNESS: single
        (D) TOPOLOGY: linear (xi) SEQUENCE DESCRIPTION: SEQ ID NO: 14

CTCCATGGTG ATAAGGTGAG TGACGATG                                         28

(2) INFORMATION FOR SEQ ID NO: 15

(i) SEQUENCE CHARACTERISTICS:
        (A) LENGTH: 18 base pairs
        (B) TYPE: nucleotides
        (C) STRANDEDNESS: single
        (D) TOPOLOGY: linear (xi) SEQUENCE DESCRIPTION: SEQ ID NO: 15

GTAAAACGAC GGCCAGTG                                                    18

(2) INFORMATION FOR SEQ ID NO: 16

(i) SEQUENCE CHARACTERISTICS:
        (A) LENGTH: 18 amino acids
        (B) TYPE: amino acids
        (C) STRANDEDNESS: single
        (D) TOPOLOGY: linear (ii) MOLECULE TYPE: peptide (vi) ORIGINAL SOURCE:
        (A) ORGANISM: Penicillum chrysogenum (xi) SEQUENCE DESCRIPTION: SEQ ID NO: 16

Met Lys Phe Ala Ser Val Leu Asn Val Leu Gly Ala Leu Thr Ala Ala Ser
              5                  10                  15

(2) INFORMATION FOR SEQ ID NO: 17

(i) SEQUENCE CHARACTERISTICS:
        (A) LENGTH: 8 amino acids
        (B) TYPE: amino acids
        (C) STRANDEDNESS: single
        (D) TOPOLOGY: linear (vi) ORIGINAL SOURCE:
        (A) ORGANISM: Penicillum chrysogenum (xi) SEQUENCE DESCRIPTION: SEQ ID NO: 17

Phe Ala Ser Val Leu Asn Val Leu
              5

(2) INFORMATION FOR SEQ ID NO: 18

(i) SEQUENCE CHARACTERISTICS:
        (A) LENGTH: 8 amino acids
        (B) TYPE: amino acids
        (C) STRANDEDNESS: single
        (D) TOPOLOGY: linear -continued

```
    (vi) ORIGINAL SOURCE:
         (A) ORGANISM: Penicillum chrysogenum (xi) SEQUENCE DESCRIPTION: SEQ ID NO: 18

Gly Ala Leu Thr Ala Ala Ser Ala
                5

(2) INFORMATION FOR SEQ ID NO: 19

(i) SEQUENCE CHARACTERISTICS:
        (A) LENGTH: 28 base pairs
        (B) TYPE: nucleotides
        (C) STRANDEDNESS: single
        (D) TOPOLOGY: linear (xi) SEQUENCE DESCRIPTION: SEQ ID NO: 19

CTCCATGGTG ACTGATTAAA CAAGGGAC                                          28

(2) INFORMATION FOR SEQ ID NO: 20

(i) SEQUENCE CHARACTERISTICS:
        (A) LENGTH: 18 base pairs
        (B) TYPE: nucleotides
        (C) STRANDEDNESS: single
        (D) TOPOLOGY: linear (xi) SEQUENCE DESCRIPTION: SEQ ID NO: 20

GTAAAACGAC GGCCAGTG                                                     18
```